US012268656B1

(12) United States Patent
Demurjian et al.

(10) Patent No.: US 12,268,656 B1
(45) Date of Patent: Apr. 8, 2025

(54) MEDICATION DISPENSING SYSTEM WITH KEYED MEDICATION CARTRIDGE

(71) Applicant: Aspargo Laboratories, Inc., New York, NY (US)

(72) Inventors: Adam Demurjian, Red Bank, NJ (US); Ravi Sawhney, Malibu, CA (US); Lance Hussey, Simi Valley, CA (US); Michael Kulick, Simi Valley, CA (US); Brian Weingarth, Woodland Hills, CA (US); Josh Probst, Culver City, CA (US); Rajvir Logani, Calabasas, CA (US); Cary Chow, Santa Monica, CA (US); Christianna Bethel, Glendale, CA (US); Craig Steel, El Segundo, CA (US); Michael Schuffert, Chatsworth, CA (US); John Vernon, Malibu, CA (US)

(73) Assignee: ASPARGO LABORATORIES, INC., New York, NY (US)

(*) Notice: Subject to any disclaimer, the term of this patent is extended or adjusted under 35 U.S.C. 154(b) by 0 days.

(21) Appl. No.: 18/600,198

(22) Filed: Mar. 8, 2024

(51) Int. Cl.
*A61J 7/00* (2006.01)
*A61J 7/04* (2006.01)
*G16H 20/13* (2018.01)

(52) U.S. Cl.
CPC .......... *A61J 7/0084* (2013.01); *A61J 7/0481* (2013.01); *G16H 20/13* (2018.01)

(58) Field of Classification Search
CPC ........ A61J 7/0084; A61J 7/0481; G16H 20/13
USPC ....................................................... 700/237
See application file for complete search history.

(56) References Cited

U.S. PATENT DOCUMENTS

| 4,549,674 | A | 10/1985 | Alticosalian |
| 5,329,976 | A | 7/1994 | Haber |
| D349,958 | S | 8/1994 | Hollis |
| 5,542,760 | A | 8/1996 | Chanoch |
| D509,296 | S | 9/2005 | Minshull |
| D650,696 | S | 12/2011 | Peden, III |
| D654,806 | S | 2/2012 | Lorenz |

(Continued)

FOREIGN PATENT DOCUMENTS

| CA | 200492 | 6/1920 |
| CA | 222464 | 8/1922 |

(Continued)

OTHER PUBLICATIONS

Non-Final Office Action, U.S. Appl. No. 18/606,136, dated May 3, 2024.

(Continued)

*Primary Examiner* — Rakesh Kumar
(74) *Attorney, Agent, or Firm* — RISSO I.P.

(57) ABSTRACT

The present disclosure provides a medication dispensing system comprised of a medication dispensing device and a keyed and associated medication cartridge. The device includes a housing containing a cartridge carrier, designed with a specific connector to align with the medication cartridge. The device also includes an authentication mechanism that works in conjunction with an activator mechanism. When operated, the activator mechanism causes the cartridge carrier to move the medication cartridge between a stored position and a dispensing position, where it can be compressed to safely and efficiently dispense medication to a user.

7 Claims, 14 Drawing Sheets

(56) References Cited

U.S. PATENT DOCUMENTS

| | | |
|---|---|---|
| D669,791 S | 10/2012 | Peden, III |
| D673,862 S | 1/2013 | Garcia |
| D693,457 S | 11/2013 | Mayer |
| D696,772 S | 12/2013 | Schneider |
| D696,964 S | 1/2014 | Chen |
| D751,415 S | 3/2016 | Otani |
| 9,501,618 B1 | 11/2016 | Wurst |
| D776,264 S | 1/2017 | Tyce |
| D778,492 S | 2/2017 | Liu |
| D801,507 S | 10/2017 | Kelnhofer |
| 9,980,140 B1 | 5/2018 | Spencer |
| D825,098 S | 8/2018 | Fornarelli |
| D827,128 S | 8/2018 | Boyaval |
| 10,127,360 B2 | 11/2018 | Chack |
| 10,204,704 B1 | 2/2019 | Wurst |
| D869,647 S | 12/2019 | Dorsey |
| D892,628 S | 8/2020 | Caruso |
| D898,900 S | 10/2020 | Atterbury |
| D912,805 S | 3/2021 | Lee-Sepsick |
| D914,514 S | 3/2021 | Wintroub |
| D918,381 S | 5/2021 | Luong |
| D921,981 S | 6/2021 | Sudlow |
| D926,968 S | 8/2021 | Kern |
| 11,154,461 B1 | 10/2021 | Abbs |
| D936,569 S | 11/2021 | Liu |
| D956,211 S | 6/2022 | Bourelle |
| D958,329 S | 7/2022 | Bourelle |
| D959,651 S | 8/2022 | Farmer |
| D962,423 S | 8/2022 | Melander |
| D968,594 S | 11/2022 | Toldi |
| D969,315 S | 11/2022 | Yamamoto |
| D973,866 S | 12/2022 | Bourelle |
| 11,517,673 B2 | 12/2022 | Pedersen |
| 11,524,115 B2* | 12/2022 | Jacobsen ............ A61M 5/2066 |
| 11,534,111 B2 | 12/2022 | Chae Kyung |
| D974,547 S | 1/2023 | O'Malley |
| 11,576,842 B2 | 2/2023 | Park |
| D980,083 S | 3/2023 | Siegel |
| 11,598,664 B2* | 3/2023 | McDermott ............ A61M 5/20 |
| 11,605,451 B2 | 3/2023 | Barbosa De Abreu E Sousa |
| 11,607,496 B2* | 3/2023 | Fabricius ............ A61M 5/2066 |
| D984,640 S | 4/2023 | Suzuki |
| 11,623,049 B2 | 4/2023 | Pedersen |
| D985,116 S | 5/2023 | Davis |
| D985,117 S | 5/2023 | Davis |
| D985,118 S | 5/2023 | Davis |
| D985,119 S | 5/2023 | Melander |
| 11,676,693 B2 | 6/2023 | Mercolino |
| 11,707,093 B2* | 7/2023 | Moloney ............... A61M 21/00 131/329 |
| 11,717,667 B2 | 8/2023 | Bochenko |
| 11,738,147 B2* | 8/2023 | Olesen ................... A61M 5/24 604/131 |
| D998,138 S | 9/2023 | Espinoza |
| D998,233 S | 9/2023 | Song |
| D1,001,272 S | 10/2023 | Boyaval |
| D1,002,838 S | 10/2023 | Dennisur |
| 11,771,591 B2* | 10/2023 | Agarwal ............... A61F 9/0008 604/298 |
| D1,010,817 S | 1/2024 | Diluzio |
| 11,865,299 B2* | 1/2024 | Estes ................... A61M 5/1723 |
| 11,872,375 B2* | 1/2024 | Plaschkes ........... A61M 5/3202 |
| 11,901,059 B2 | 2/2024 | Pugsley |
| 11,929,160 B2* | 3/2024 | Edwards ................ G16H 20/17 |
| 11,931,552 B2* | 3/2024 | Bar-El ............. A61M 5/14244 |
| D1,025,471 S | 4/2024 | Tao |
| 11,980,739 B2 | 5/2024 | Pizzochero |
| 11,998,057 B2* | 6/2024 | Moloney ................ A24F 40/57 |
| 12,005,241 B2* | 6/2024 | Pedersen ............ A61M 5/3158 |
| 12,042,614 B2 | 7/2024 | Johnston |
| D1,038,381 S* | 8/2024 | Demurjian ................ D27/101 |
| 12,053,615 B2* | 8/2024 | Estes ................... A61M 5/1413 |
| 12,064,591 B2* | 8/2024 | Estes ................... G16H 20/17 |
| 12,106,836 B1 | 10/2024 | Demurjian |
| 2002/0169635 A1 | 11/2002 | Shillingburg |
| 2003/0216831 A1 | 11/2003 | Hart |
| 2005/0073832 A1 | 4/2005 | Shilton |
| 2006/0027233 A1 | 2/2006 | Zierenberg |
| 2009/0294521 A1 | 12/2009 | De La Huerga |
| 2009/0302062 A1 | 12/2009 | Maddy |
| 2010/0211005 A1* | 8/2010 | Edwards ............ A61M 15/008 604/82 |
| 2011/0000170 A1 | 1/2011 | Burg |
| 2011/0168175 A1 | 7/2011 | Dunne |
| 2012/0035546 A1 | 2/2012 | Cabiri |
| 2013/0090594 A1* | 4/2013 | Palmer ................ A61J 7/0053 604/60 |
| 2013/0211327 A1 | 8/2013 | Osman |
| 2013/0221097 A1* | 8/2013 | Day ....................... A61M 5/20 235/437 |
| 2013/0245604 A1* | 9/2013 | Kouyoumjian ... A61M 5/31546 604/506 |
| 2013/0253433 A1 | 9/2013 | Senior |
| 2014/0323883 A1 | 10/2014 | Fahey |
| 2014/0323963 A1* | 10/2014 | West ................... A61M 5/3294 604/82 |
| 2014/0326238 A1 | 11/2014 | Spandorfer |
| 2015/0257979 A1 | 9/2015 | Jenema |
| 2015/0288797 A1 | 10/2015 | Vincent |
| 2015/0364057 A1 | 12/2015 | Catani |
| 2017/0007763 A1* | 1/2017 | McLoughlin ........... A61M 5/20 |
| 2017/0053098 A1 | 2/2017 | Hawkins |
| 2017/0091392 A1 | 3/2017 | White |
| 2017/0277937 A1 | 9/2017 | Baek |
| 2017/0283151 A1 | 10/2017 | Stormer |
| 2017/0326033 A1 | 11/2017 | Kraft |
| 2018/0342329 A1 | 11/2018 | Rufo |
| 2018/0369070 A1 | 12/2018 | Gielen |
| 2019/0001085 A1 | 1/2019 | Cottenden |
| 2019/0240430 A1 | 8/2019 | Jackson |
| 2020/0022416 A1* | 1/2020 | Alarcon ................ A61M 15/08 |
| 2020/0022418 A1 | 1/2020 | Belisle |
| 2020/0187565 A1* | 6/2020 | Williams ............. A61M 11/005 |
| 2020/0360239 A1 | 11/2020 | Campos |
| 2020/0384198 A1 | 12/2020 | Becker |
| 2020/0384216 A1* | 12/2020 | Eicher ............... A61M 15/0068 |
| 2021/0030626 A1 | 2/2021 | Medhal |
| 2021/0104304 A1 | 4/2021 | Davidovics |
| 2021/0146066 A1* | 5/2021 | Wuttke .................. A61M 11/02 |
| 2021/0154417 A1 | 5/2021 | Cheng |
| 2021/0236752 A1 | 8/2021 | Botha |
| 2021/0257068 A1 | 8/2021 | Emmanuel |
| 2021/0264716 A1 | 8/2021 | Norbeck |
| 2021/0290491 A1 | 9/2021 | Campos |
| 2021/0319782 A1 | 10/2021 | Gong |
| 2021/0361879 A1 | 11/2021 | Gjertsen |
| 2021/0378916 A1* | 12/2021 | Shalon .................. A61J 7/0418 |
| 2022/0131699 A1 | 4/2022 | Kimmel |
| 2022/0269763 A1 | 8/2022 | Lett |
| 2022/0287915 A1 | 9/2022 | Lebrun |
| 2022/0379046 A1* | 12/2022 | Decock ................. A61M 15/08 |
| 2023/0036333 A1 | 2/2023 | Park |
| 2023/0065458 A1 | 3/2023 | Abadi |
| 2023/0248614 A1 | 8/2023 | Aon |
| 2023/0321372 A1 | 10/2023 | Fabien |
| 2024/0090588 A1 | 3/2024 | Barbaric |

FOREIGN PATENT DOCUMENTS

| | | | |
|---|---|---|---|
| WO | 2012013723 A1 | 2/2012 | |
| WO | WO-2012109222 A2 * | 8/2012 | ................ A61J 1/03 |
| WO | 2016205609 A1 | 12/2016 | |
| WO | WO-2022165349 A1 * | 8/2022 | ................ A61J 1/03 |

OTHER PUBLICATIONS

"Medication Dispense and Monitoring System using Biometric Fingerprint-Recognition Authentication," An IP.com Prior Art Database Technical Disclosure; Authors et. al.: IBM; Original Publication Date: Aug. 29, 2003; IP.com No. PCOM000019130D; IP.com Electronic Publication Date: Aug. 29, 2003 (Year: 2003).

Flonq Max Smart Disposable Vape, Fiona, [Postdate unknown],

(56) References Cited

OTHER PUBLICATIONS

[Site seen: May 13, 2024], Seen at URL: https://www.flonq.global/blog-news/flonq-max-smart-disposable-vape-top-notch-tech-meets-impressive-performance-in-2024 (Year: 2024).
Lauren Golik, "Can We Pump the Brakes on Pumps?", Beauty Independent, Jul. 25, 2020.
Mole, Beth, "E-cig co. put Viagra, Cialis in vape liquids—the FDA is throbbing mad," Ars Technica, [Post date: Oct. 12, 2018], [Site seen: May 13, 2024], Seen at URL: https://arstechnica.com/science/2018/10/ fda-issues-stiff-warning-to-e-cig-seller-who-put-viagra-in-vape-liquid/ (Year: 2018).
Notice of Allowance dated Jun. 21, 2024 for U.S. Appl. No. 18/606,136 (pp. 1-3).
Notice of Allowance dated Jun. 27, 2024 for U.S. Appl. No. 18/606,136 (pp. 1-2).
Notice of Allowance dated Jul. 8, 2024 for U.S. Appl. No. 18/606,136 (pp. 1-2).
Office Action dated May 3, 2024 for U.S. Appl. No. 18/606,136 (pp. 1-8).
Office Action dated Jun. 27, 2024 for U.S. Appl. No. 18/655,722 (pp. 1-10).
Office Action dated Jul. 3, 2024 for U.S. Appl. No. 18/601,329 (pp. 1-11).
Office Action dated Jul. 31, 2024 for U.S. Appl. No. 18/600,402 (pp. 1-9).
Office Action dated Jun. 3, 2024 for U.S. Appl. No. 18/614,041 (pp. 1-22).
Office Action dated May 22, 2024 for U.S. Appl. No. 18/614,085 (pp. 1-9).
Office Action dated May 29, 2024 for U.S. Appl. No. 18/614,062 (pp. 1-23).
Office Action dated May 30, 2024 for U.S. Appl. No. 18/606,151 (pp. 1-10).
Patil et al., "An IoT based Smart Medicine Dispenser Model for Healthcare," 2022 IEEE World Conference on Applied Intelligence and Computing; Doi: 10.1109/AIC55036.2022.9848934. (Year: 2022).
Perez et al., Evaluation of a Tracking System for Patients and Mixed Intravenous Medication Based on RFID Technology, Nov. 30, 2016, Sensors, pp. 1-15. (Year: 2016).
Shanthini et al., "Design and Implementation of IoT based Automatic Medicine Dispenser for Patients," Proceedings of the Third International Conference on Innovative Mechanisms for Industry Applications (ICIMIA 2023); DOI: 10.1109/ICIMIA60377.2023.10426176. (Year: 2023).
Sildenafil Spray, Aspargo Labs, [post date unknown], [site seen May 13, 2024], Seen at URL: https://aspargolabs.com/ (Year: 2024).
Notice of Allowance dated Aug. 14, 2024 for U.S. Appl. No. 18/606,136 (pp. 1-2).
Office Action (Non-Final Rejection) dated Oct. 23, 2024 for U.S. Appl. No. 18/606,173 (pp. 1-11).
Office Action dated Aug. 29, 2024 for U.S. Appl. No. 18/614,085 (pp. 1-12).
Office Action dated Sep. 11, 2024 for U.S. Appl. No. 18/614,041 (pp. 1-27).
Office Action dated Sep. 11, 2024 for U.S. Appl. No. 18/614,062 (pp. 1-21).
Office Action dated Nov. 13, 2024 for U.S. Appl. No. 18/601,329 (pp. 1-17).
Office Action dated Nov. 13, 2024 for U.S. Appl. No. 18/655,722 (pp. 1-8).
Office Action dated Nov. 18, 2024 for U.S. Appl. No. 18/600,402 (pp. 1-8).
International Search Report and Written Opinion issued in App. No. PCT/US2024/047468, dated Dec. 11, 2024, 8 pages.
International Search Report and Written Opinion issued in App. No. PCT/US2024/047482, dated Dec. 12, 2024, 9 pages.
International Search Report and Written Opinion issued in App. No. PCT/US2024/047497, dated Dec. 11, 2024, 8 pages.
International Search Report and Written Opinion issued in App. No. PCT/US2024/047676, dated Jan. 27, 2025, 7 pages.
International Search Report and Written Opinion issued in App. No. PCT/US2024/047686, dated Dec. 11, 2024, 8 pages.
International Search Report and Written Opinion issued in App. No. PCT/US2024/047694, dated Dec. 11, 2024, 8 pages.
Office Action dated Feb. 5, 2025 for U.S. Appl. No. 18/606,173 (pp. 1-10).

* cited by examiner

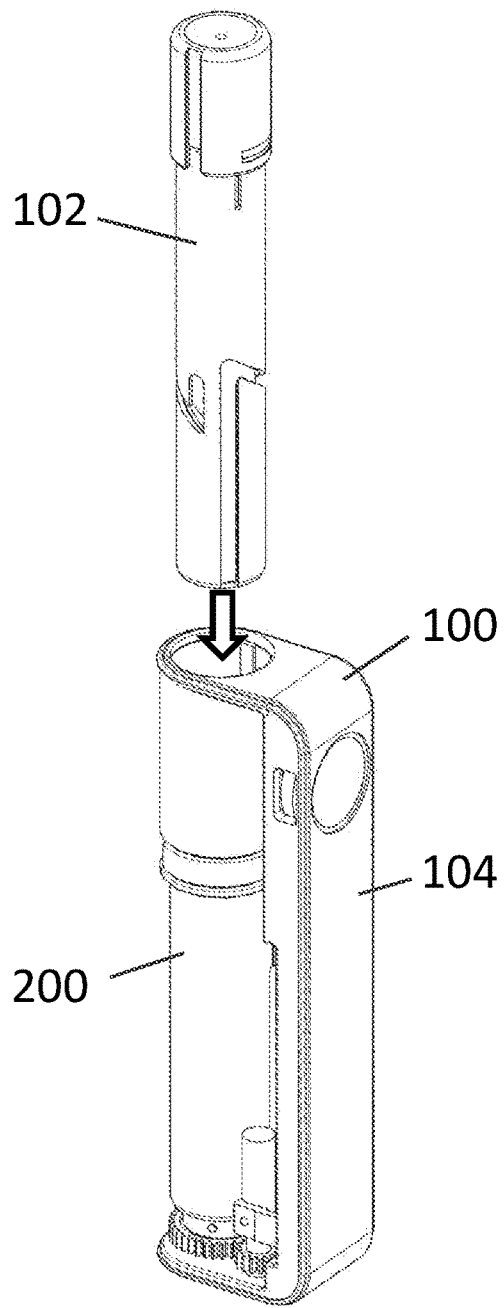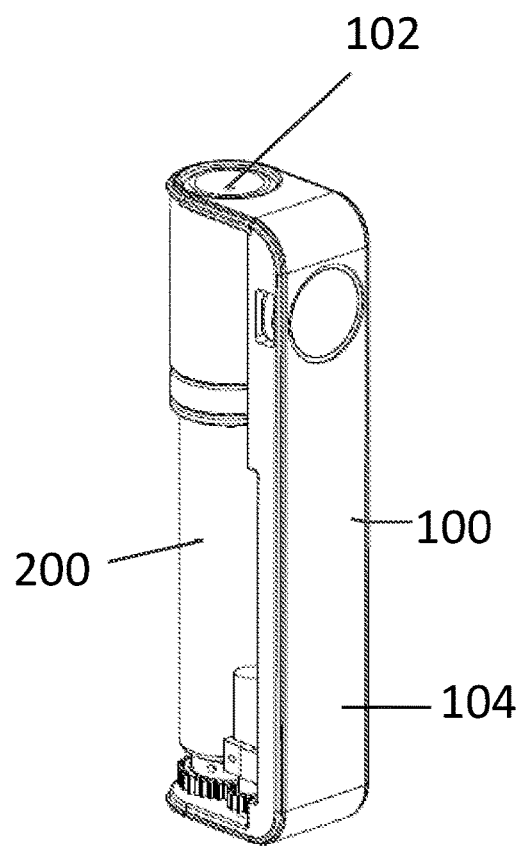
FIG. 2A
FIG. 2B

102

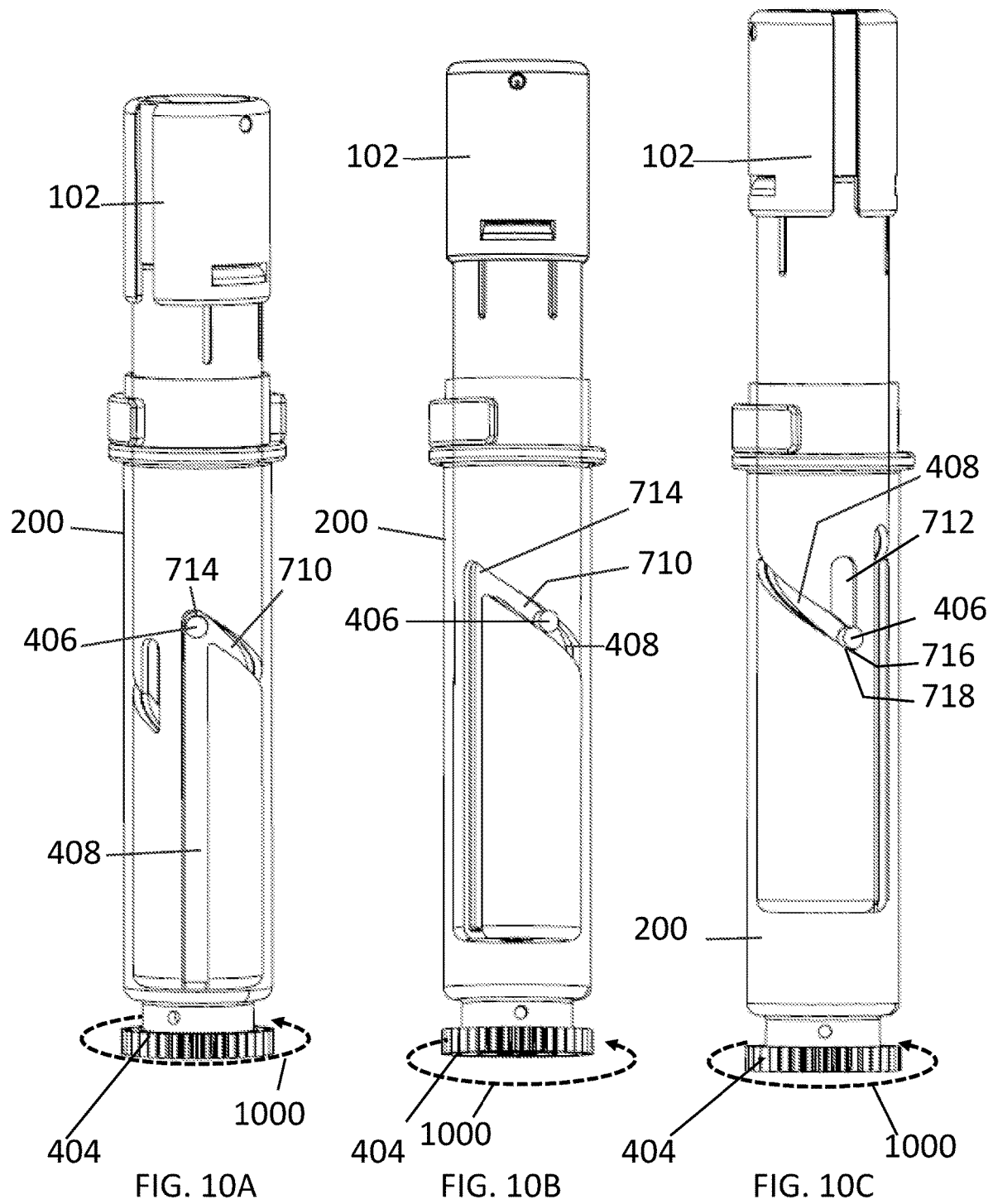

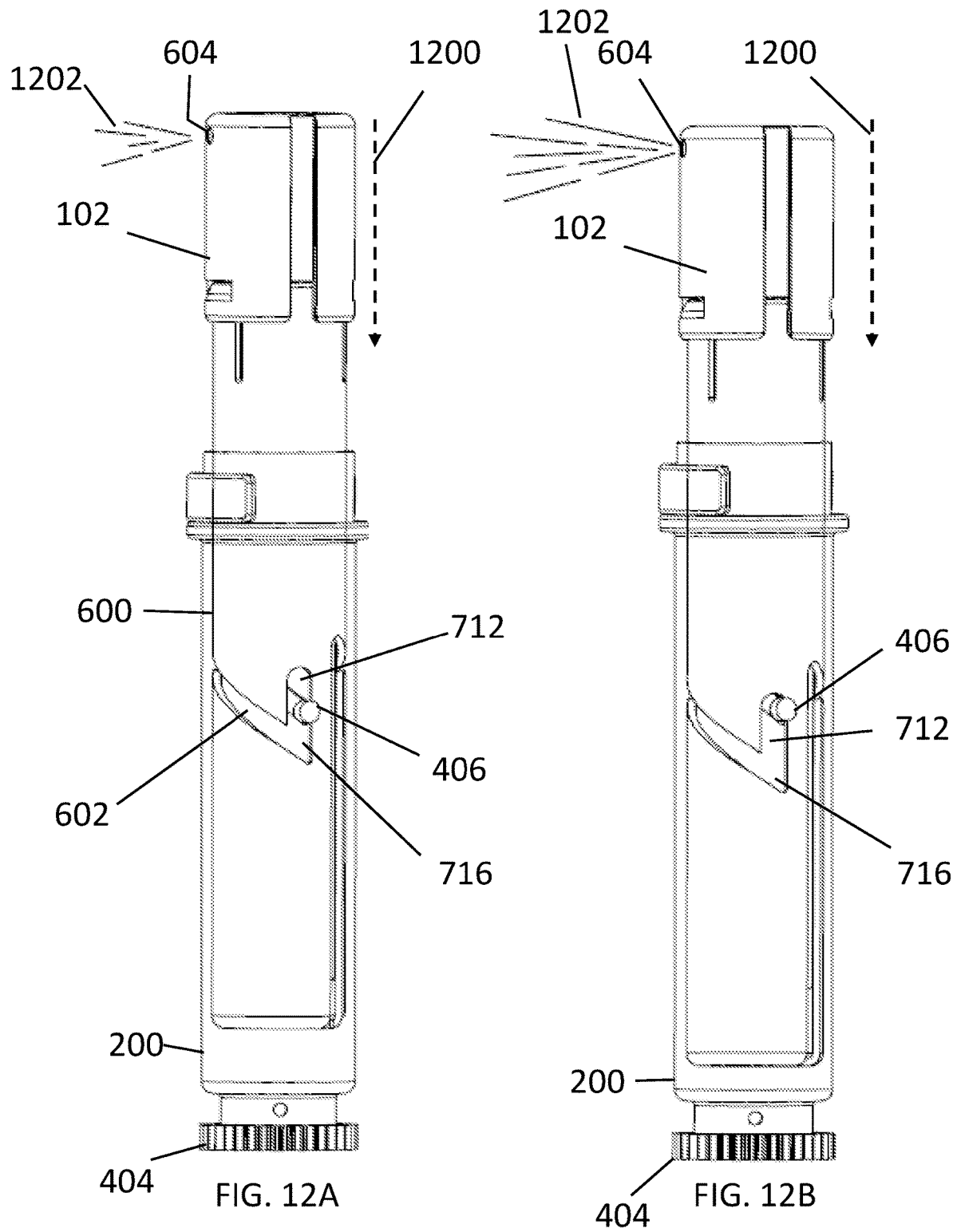

MEDICATION DISPENSING SYSTEM WITH KEYED MEDICATION CARTRIDGE

BACKGROUND OF THE INVENTION

(1) Field of Invention

The present invention relates to a medication dispensing system and, more particularly, to a handheld oral medication dispensing device and associated medication cartridge.

(2) Description of Related Art

The field of medication treatment has grown increasingly complex in recent years, with patients frequently needing to manage and administer multiple types of medication. Under such circumstances, it is vital to provide reliable, accessible, and simple methodologies to patients for dispensing their medications. Many existing dispensing devices, however, tend to be cumbersome, confusing, or inefficient. Often, they rely on patients having to manually change their medication reminders or products, which can involve complicated steps or create potential for mistakes, like grabbing the wrong medication or dispensing an incorrect dosage. Furthermore, mistakes may potentially have serious health implications. Hence, it is vital to design an easy-to-use and fail-safe medication dispensing device.

Further, existing oral medications are typically taken as tablets or syrups. Such medication delivery items may be functional, but often take time for efficacy due to digestive and other body related functions. Additionally, such medication delivery techniques are inconvenient to carry on ones person or inconspicuously use. Thus, a need exists for a unique oral medication dispensing device and keyed medication cartridge that provides an alternative to tablet and syrup-type medications.

SUMMARY OF INVENTION

The present disclosure provides a medication dispensing system that is comprised of a handheld oral medication dispensing device and associated medication cartridge. One embodiment disclosed herein pertains to the handheld oral medication dispensing device with an automatic cartridge activator mechanism. The purpose of this design is not only to make medication administration simpler and more efficient but also to mitigate potential errors associated with manual cartridge switching. The device provides user authentication and employs a simple yet effective actuation mechanism to operate, further enhancing safety measures. The innovative design of the keyed connector and the configuration of the cartridges can significantly aid patients manage and administer their medication effectively and safely.

In one aspect, the medication dispensing device has a housing with a cartridge carrier therein, the cartridge carrier having a keyed connector that is keyed to a medication cartridge to allow for insertion and alignment of the medication cartridge within the cartridge carrier. Further, in another aspect, an activator mechanism is positioned within the housing, the activator mechanism operably connected with the cartridge carrier to cause the cartridge carrier to actuate, whereby upon actuation of the cartridge carrier, the cartridge carrier selectively moves an inserted medication cartridge between a stored position and a dispensing position.

In yet another aspect, the cartridge carrier is rotatable within the housing.

In another aspect, the cartridge carrier includes a proximal end and a distal end, the proximal end being open for receiving the medication cartridge therein, while the distal end includes a gear wheel operably connected to the activator mechanism.

In yet another aspect, the activator mechanism includes at least a battery, a motor, and one or more gears that are operably connected to the gear wheel, such that activation of the activator mechanism causes the motor to turn the one or more gears and, in doing so, turn the gear wheel and rotate the cartridge carrier.

In yet another aspect, the keyed connector includes one or more alignment features that protrude into the cartridge carrier.

In another aspect, the medication cartridge is included and formed to be inserted within the cartridge carrier.

In another aspect, the medication cartridge is an elongated cartridge with one or more alignment channels that align with and receive the one or more alignment features.

In yet another aspect, the one or more alignment channels includes a pair of opposing channels, while the one or more alignment features are a pair of opposing protrusions that slide within the pair of opposing channels.

Further, the medication cartridge is comprised of a shell having a dispensing aperture and a vial slidably positioned within the shell, the vial having a pump assembly with an outlet aligned with the dispensing aperture.

In another aspect, the vial is slidable within the shell between an expanded state and a compressed state, such that when transitioning to the compressed state, the pump assembly is actuated to pump medicine from the outlet and through the dispensing aperture.

In yet another aspect, the shell includes a pair of opposing slots that align with the pair of opposing channels such that the pair of opposing protrusions pass through the pair of opposing slots and into the pair of opposing channels.

In another aspect, the medication cartridge has a bottom end and a top end, such that each of the pair of opposing slots has a first slot that rises upward from the bottom end toward the top end to a first junction, and then a second slot that traverses downward at an angle from the first junction toward a second junction, and then a third slot that rises upward again from the second junction toward the top end.

In yet another aspect, each of the pair of opposing channels rises upward from the bottom end toward the top end to the first junction, and then traverses downward at an angle from the first junction toward the second junction, where each of the pair of opposing channels terminates in a channel terminal.

In another aspect, when the medication cartridge is within the cartridge carrier in the stored position, the pair of opposing protrusions rest within the first junction.

In yet another aspect, activation of the activator mechanism causes a rotation of the cartridge carrier, thereby causing the pair of opposing protrusions to travel through the pair of opposing slots and the pair of opposing channels from the first junction to the second junction and, in doing so, lift the medication cartridge from the cartridge carrier from the stored position to the dispensing position.

Further, when in the dispensing position, the pair of opposing protrusions pass through the pair of opposing slots and into the pair of opposing channels at the second junction and rest within the channel terminals.

In yet another aspect, the medication cartridge is formed such that depression of the top end of the medication cartridge forces the shell downward while the pair of opposing protrusions pass through the third slots while remaining affixed within the channel terminals, thereby forcibly sliding the vial within the shell from the expanded state to the compressed state and actuating the pump assembly.

In yet another aspect, the dispensing device further comprises an authentication mechanism operably connected with the activator mechanism, the authentication mechanism operable for authenticating a user and, when authenticated, activating the activator mechanism to cause the cartridge carrier to actuate and move the inserted medication cartridge from the stored position to the dispensing position.

Finally, as can be appreciated by one in the art, the present invention also comprises a method for forming and using the invention as described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 2A shows an interior-view of the medication dispensing device, depicting a cartridge carrier;

FIG. 2B shows an interior-view of the medication dispensing device, depicting the medication cartridge inserted into the cartridge carrier;

FIG. 10A shows an exemplary illustration of the medication cartridge inserted into the cartridge carrier, depicting the medication cartridge in a stored position;

FIG. 10B shows an exemplary illustration of the medication cartridge inserted into the cartridge carrier, depicting the cartridge carrier rotating to move the medication cartridge up and toward the dispensing position;

FIG. 10C shows an exemplary illustration of the medication cartridge inserted into the cartridge carrier, depicting the cartridge carrier as rotated to move the medication cartridge up and into the dispensing position;

FIG. 12A shows an exemplary illustration of the medication cartridge within the cartridge carrier, depicting the medication cartridge in the dispensing position and being pressed downward to activate the pump assembly and dispense medication from the medication cartridge; and FIG. 12B shows an exemplary illustration of the medication cartridge within the cartridge carrier, depicting the medication cartridge in the dispensing position and being pressed downward to activate the pump assembly and dispense medication from the medication cartridge.

DETAILED DESCRIPTION

Figure 1:
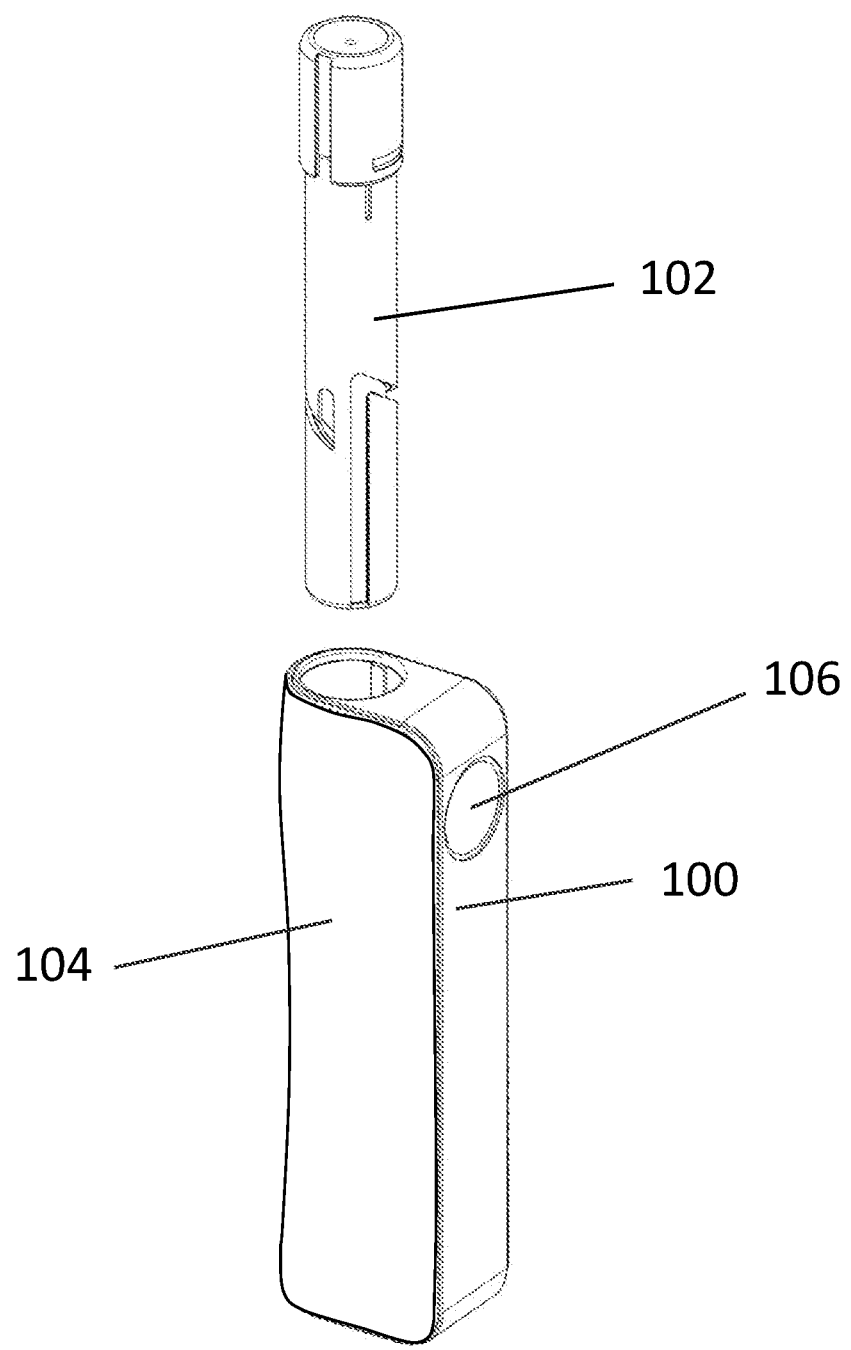
FIG. 1 shows an exemplary illustration a handheld medication dispensing device and medication cartridge according to various embodiments of the present invention.

The present invention relates to a medication dispensing system and, more particularly, to a handheld oral medication dispensing device and associated medication cartridge. It should be noted that the dispensing device and associated medication cartridge are described herein as having several features and functions and, importantly, that the dispensing device and medication cartridge include any components, parts, etc. as understood by those skilled in the art and as may be necessary to implement said features and functions, including any electrical components, integrated circuits and/or microprocessors, etc.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

As noted above, the present invention relates to a medication dispensing system that is comprised of a handheld oral medication dispensing device and an associated and keyed medication cartridge. As shown in FIG. 1, the handheld medication dispensing device 100 is designed primarily to securely store and dispense medication from a medication cartridge 102. The device 100 comprises a housing 104, principally structured to protect the critical internal components while offering ergonomic suitability for handheld operation. The housing 104 exterior is designed with both convenience and comfort in mind, allowing a user to hold the device 100 and access the medication with ease. In an exemplary embodiment, the housing 104 may be configured in a variety of shapes, sizes, and materials to accommodate different user preferences and medication types.

In one embodiment, the device 100 includes an authentication mechanism 106 that is designed to authenticate a user's identification in various manners. The authentication mechanism 106 is any suitable mechanism, device, system, etc., that allows for user authentication, non-limiting examples of which include biometrics (such as fingerprint reader or facial recognition via a camera and app, etc.), a password or passcode system, a security token, or any other known authentication method or device. The authentication mechanism 106 is set up to permit the authenticated or designated user access to the operation of the said device 100, thereby ensuring a highly secure and personal way of dispensing medication. In one embodiment and as illustrated, the authentication mechanism 106 includes a fingerprint reader and all associated components as necessary to allow for authentication with such a reader, including an integrated circuit, power (battery), etc. For example, in a first use, the authentication mechanism 106 can be configured to recognize the user and thereafter only allow access to the recognized user. Such a setup can be configured in any suitable manner as understood by those skilled in the art. As non-limiting example, a first use may require that a user place a finger on the authentication mechanism 106 which turns on the device 100 and provides indicia (e.g., via a light, digital screen, etc.) to notify the user to place their finger on the fingerprint reader. The fingerprint reader then reads and stores the fingerprint of the designated user. Thereafter, the activator mechanism can only be activated by the designated user upon placement of the finger on the fingerprint reader. In another example, software or a phone application can be used to wirelessly communicate (e.g., via Wi-Fi, Bluetooth, etc.) with the device 100 to program the device to only recognize the designated user via the authentication mechanism. In this aspect, the device 100 includes all necessary components to allow it to wirelessly communicate with an external device, non-limiting examples of which include Wi-Fi transceivers/components, Bluetooth components/gear, etc. In an alternative embodiment, the device 100 can simply be turned off and on (without an authentication mechanism), and includes a button or other similar feature to cause the device 100 to operate and actuate the activation mechanism as described in further detail below.

In one aspect, the authentication mechanism 106 is a biometric fingerprint reader linked to a mobile app, which can be used to prevent unauthorized medication dispensing, requiring user authorization via the app for initialization, and connecting to caregivers and personal networks to ensure medication adherence. The design of the device 100, accessories, and app is centered around the need for an easier and better way to receive the right dose, at the right time, in the right way and frequency. In one aspect, controlled via the app, the handheld device 100 can alert users to their medication schedule, while also notifying caregivers and family members about adherence. For restricted medications, the device 100 and associated app can restrict dosing until authorized by the prescribing physician. Tampering with the medication cartridge 102 triggers alerts to caregivers, pharmacists, and physicians, ensuring safe usage, especially for restricted medications by alerting through the app that the medication has not been taken as prescribed. In another aspect, the device 100 and medication cartridge 102 are formed to include any necessary components that allow the device 100 to recognize a specific medication cartridge 102. As a non-limiting example, each medication cartridge 102 can be formed to include a Radio Frequency Identification (RFID) tag, while the device 100 includes an RFID reader (or other similar technology).

As shown in the interior views of FIGS. 2A and 2B, integrated within the housing 104 is a cartridge carrier 200. The cartridge carrier 200 functions as a receptacle for the medication cartridge 102. The cartridge carrier 200 includes a keyed connector, most importantly, innovatively designed to align with a specified type of medication cartridge 102. This keyed connector serves as an interlocking structure that carefully guides the positioning and orientation of the cartridge 102, allowing only for the insertion of a compatible medication cartridge 102. The keyed connector along with the cartridge carrier 200 ensure the correct placement and alignment of the medication cartridge 102, which can help eliminate potential misuse or cartridge damage, and fostering a smooth transition between stored and dispensing positions (as described in further detail below).

Figure 3:
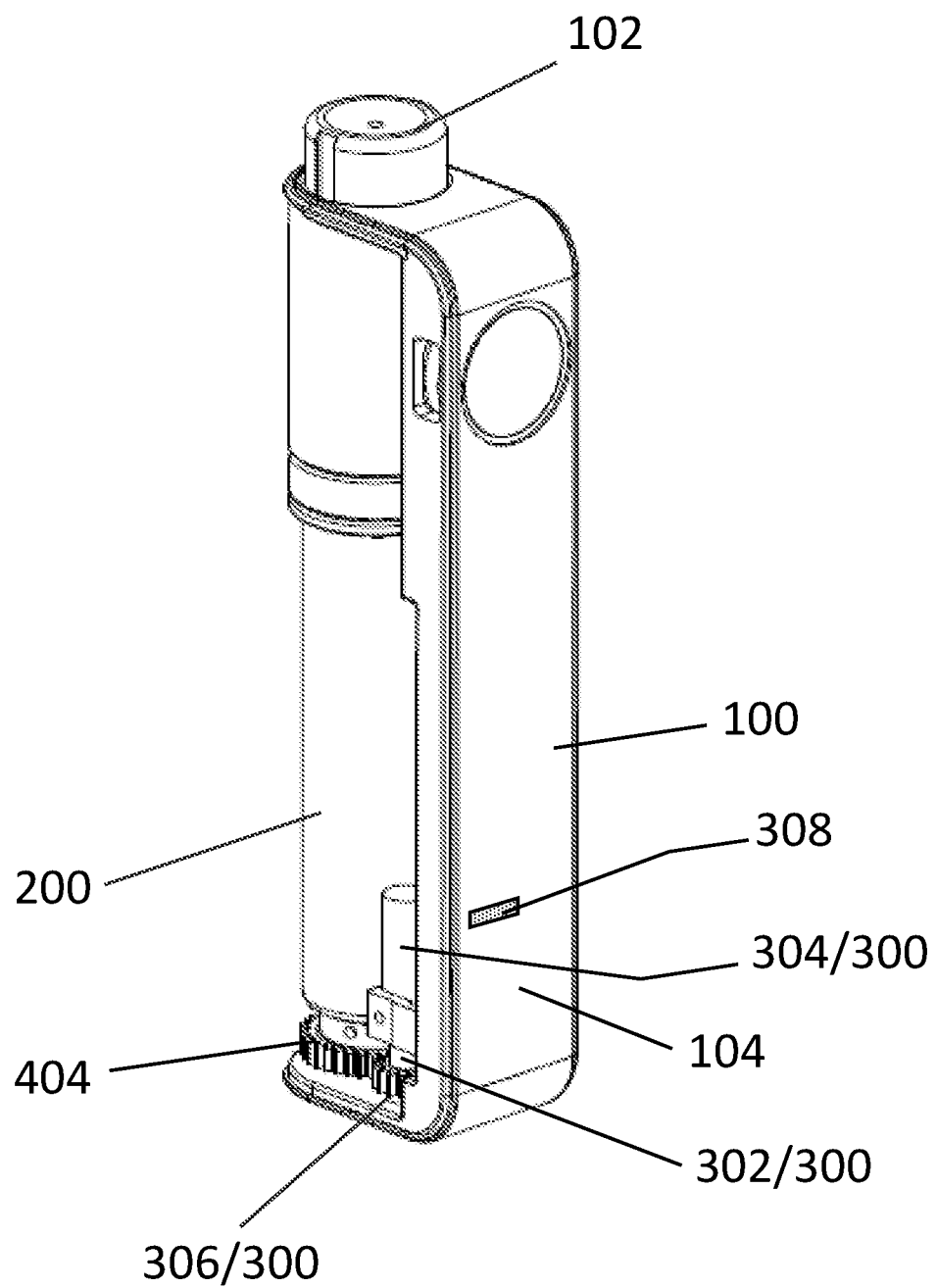
FIG. 3 is an interior-view illustration of the medication dispensing device, depicting an activator mechanism as operably connected with the cartridge carrier.

As shown in the interior view of FIG. 3, an activator mechanism 300 forms part of the configuration and is integrated within the housing 104. The activator mechanism 300, when engaged, prompts the cartridge carrier 200 to actuate. The involvement of the activator mechanism 300 ensures a controlled movement of the inserted medication cartridge 102 between two positions-a stored position and a dispensing position. Note that FIG. 2A depicts the medication cartridge in a stored position, while FIG. 3 depicts the medication cartridge in a dispensing position.

In the stored position, as shown in FIG. 2A, the medication is kept secure within the device 100. The position ensures safety by preventing unintentional discharge of medication when not in use. When the activator mechanism 300 is activated, the cartridge carrier 200 rotates to lift up the medication cartridge 102 into the dispensing position. When this dispensing position is selected, the medication cartridge 102 is correctly oriented to dispense the medication through a dispensing aperture (described in further detail below) integrated into the medication cartridge 102.

The link between the activator mechanism 300 and the cartridge carrier 200 allows for reliable and essential movement control. This means the user can confidently operate the device 100 knowing the medication is dispensed accurately and safely.

The cartridge carrier 200 is formed in any suitable manner to allow for activation by the activator mechanism 300, which results in transitioning the medication cartridge 102 between the stored and dispensing positions. In an embodiment and as shown in FIG. 3, the cartridge carrier 200 is rotatable within the housing 104. The cartridge carrier 200 may be formed of materials that possess strength and durability such as, but not limited to, metals, polymers, and/or composites. The size, shape, and dimensions of the cartridge carrier may vary as per the application requirements.

The housing 104 may be constructed to accommodate the rotatable cartridge carrier 200. The construction of the housing 104 can also encompass different types of materials that provide the necessary strength and durability inclusive of, but not limited to metals, polymers, composites, among others. The interior of the housing 104 is ideally designed to allow the cartridge carrier 200 to rotate through actuation of the activator mechanism 300.

The activator mechanism 300, ensuring the cartridge carrier's 200 rotation within the housing 104, can be implemented through a variety of means, such as mechanical gears, electric motors, a battery, manually operated mechanisms, integrated circuits, or any combination thereof. This activator mechanism 300 administration permits the user to precisely position the cartridge carrier 200 within the housing 104 between a first position (in which the medication cartridge 102 is inserted into the cartridge carrier 200 and is stored in a stored position) and a second position (in which the medication cartridge 102 is lifted from the housing 104 to a dispensing position). The activator mechanism 300 can then be activated to rotate the cartridge carrier 200 in an opposite direction to return the medication cartridge 102 to the stored position.

In one aspect, the dispensing device 100 includes a locking mechanism that is configured to selectively lock/unlock the mediation cartridge 102 within the cartridge carrier 200. The locking mechanism may involve an interlocking system, a magnetic attachment, or any other secure attachment mechanism. As a non-limiting example, the locking mechanism may be a spring-loaded detent style 'click-in' and 'click-out' mechanism formed at the bottom of the medication cartridge 102 and cartridge carrier 200. In another aspect, the locking mechanism can be an electronically actuated lock (e.g., mechanized tab, etc.) that locks the medication cartridge 102 into the cartridge carrier 200. For example, the exterior surface of the medication cartridge can include a slot that is formed to accommodate a tab that is electronically moved (e.g., turned/slid, etc.) into the slot when locking and, in the alternative, pulled from the slot when released. As yet another non-limiting example, the locking mechanism can include programming such that after the cartridge 102 is inserted into the cartridge carrier 202, the cartridge carrier 200 is rotate partially until alignment features (described in further detail below and depicted as element 406) are positioned in the middle of the second slot (described in further detail below and depicted as element 710), with the cartridge carrier 200 then stopped until it is desired to rotate further to position the medication cartridge 102 in the dispensing position. With the alignment features in the middle of the second slot, the cartridge 102 is effectively locked within the cartridge carrier 200. Thus, as can be appreciated by those skilled in the art, there are several mechanisms that can be employed to selectively lock the medication cartridge 102 into the cartridge carrier 200.

In another aspect, the inclusion of the locking mechanism may also be included to secure the cartridge carrier 200 at any desired rotational position, thus preventing unintentional and unwanted movement when the cartridge carrier 200 is set in a particular position. This locking mechanism can be integrated into the cartridge carrier 200, the housing 104, the activator mechanism 300, or combinations of these components. This rotatable cartridge carrier 200 system installed within a housing 104 assembly may have wide ranging applications, such as, for instance, accommodating various cartridges for providing users with quick and easy access to different medications and dosages, multiple configurations, interchangeability of components, and more. Thus, the present one embodiment discloses a rotatable cartridge carrier 200 system, promoting case of use, enhancing performance, providing efficient operation, flexibility, improved control and precision, leading to a more efficient and user-friendly functionality.

Figure 4:
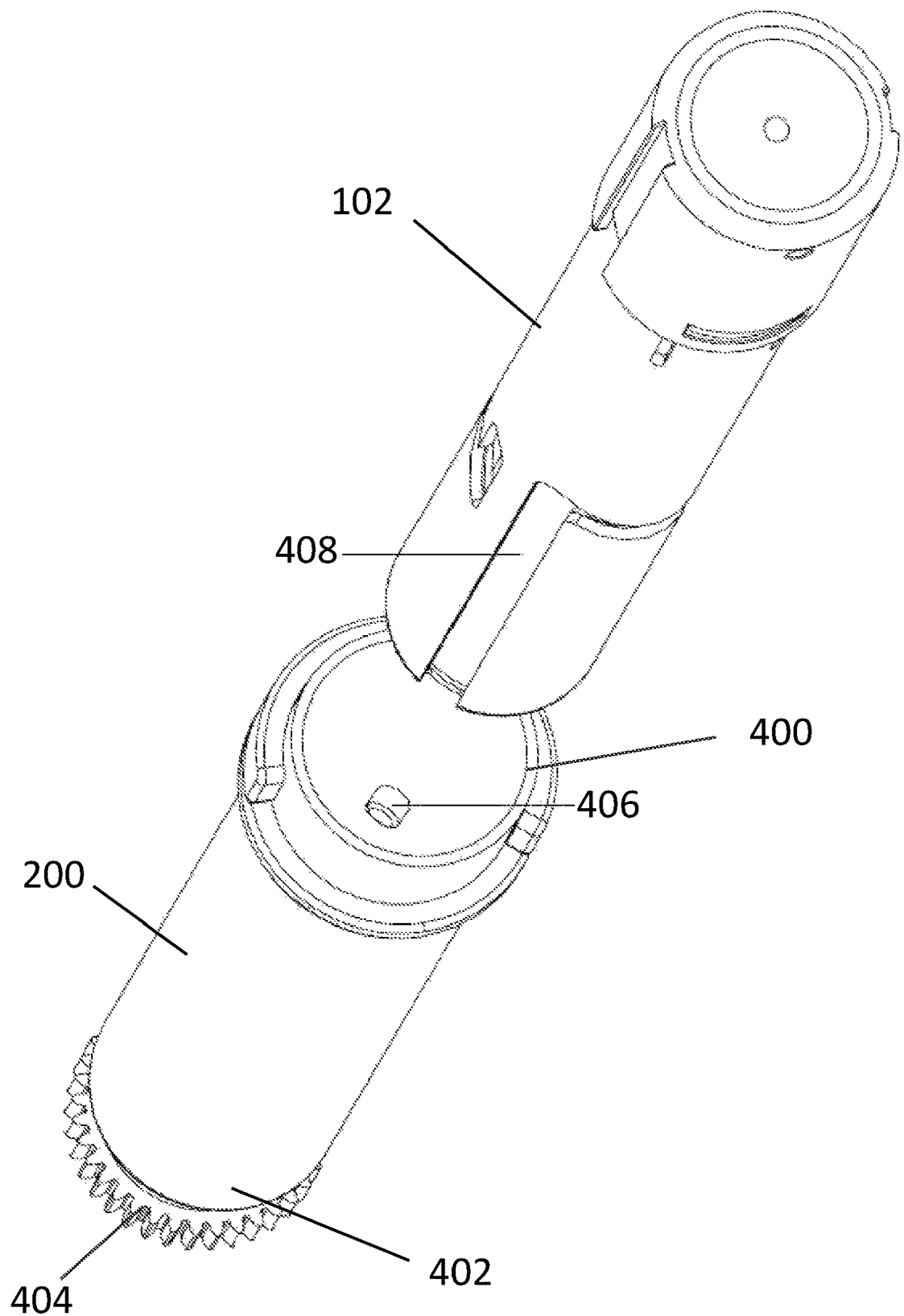
FIG. 4 shows an exemplary illustration of the cartridge carrier and medication cartridge.

In one embodiment and as shown in FIG. 4, the cartridge carrier 200 includes both a proximal end 400 and a distal end 402. The proximal end 400 of this unit is open, and it is specifically structured to receive the medication cartridge 102. This can be any kind of medication cartridge 102, and the open design simplifies the process of interchanging cartridges of differing medications, volumes, or other specifications, thus making it broadly applicable and versatile.

The distal end 402 of the cartridge carrier 200 includes a key component of this one embodiment-a gear wheel 404. This gear wheel 404 is not a mere inclusion but is operably connected to the activator mechanism 300. The gear wheel 404 and activator mechanism 300 are conceptually designed to work in harmony. In operation, when the user deploys the activator mechanism 300, the included gear wheel 404 is rotated, thereby rotating the cartridge carrier 200.

The gear wheel 404 is a significant element in the functioning of this device 100 mainly due to its interaction with the activator mechanism 300. The gear wheel 404, upon the interaction with activator mechanism 300, contributes to the precision with which the cartridge carrier 200 is rotated to position the medication cartridge 102 between the stored and dispensing positions. Its size, teeth count, and interaction with other gears if connected, contribute to its function.

Moreover, the position of the gear wheel 404 at the distal end 402 of the cartridge carrier 200 may also assist in a user-friendly, ergonomic design. The gear wheel's 404 location ensures a seamless connection between the mechanical parts of the activator mechanism 300 and the carrier cartridge 200, augmenting the device's 100 overall performance.

As noted above and referring again to FIG. 3, the device 100 includes an activator mechanism 300 to selectively turn the gear wheel 404 and, by extension, rotate the cartridge carrier 200. The activator mechanism 300 includes any components as necessary to rotate the gear wheel 404. In one embodiment, the activator mechanism 300 comprises of at least a battery 304, a motor 302, and one or more gears 306 that are operably connected to the gear wheel 404. The battery in the device 100 forms the power source, capable of providing a stable and reliable supply of power to the other components. The size, capacity, and type of the battery 304 may be customized according to design preferences, device requirements, or various other factors, while being compliant with standard safety and operation guidelines. In some aspects, the battery 304 is encased within the device 100 and intended for device 100 replacement upon depletion of the battery 304, while in other aspects, it is replaceable. In yet other aspects, the battery 304 is rechargeable using a charging port 308 or any other charging means as known to those skilled in the art.

The motor 302 functions as the primary mechanical component that is responsible for movement or force in the device 100. Upon activation, the motor 302 draws power from the battery and begins to turn to rotate any of the one or more gears and the operably connected gear wheel 404. The type, size, and characteristics of the motor 302 can be adjusted based on the requirements of the device, anticipated load, desired performance factors among other parameters.

The one or more gears represent a transmission mechanism, operably connected to the motor 302 and the gear wheel 404. Upon the activation of the device 100, the rotational force produced by the motor 302 is transferred to these gears. The gears enable the transfer of power from the motor 302 to the gear wheel 404. Upon receiving the force from the one or more gears of the activator mechanism 300, the gear wheel 404 begins to turn. This turning of the gear wheel 404 then contributes to the rotation of a cartridge carrier 200.

Referring again to FIG. 4, one embodiment pertains to an enhanced cartridge carrier 200 system, specifically designed with one or more alignment features 406 that protrude into the cartridge carrier 200 for a keyed connection and accurate cartridge 102 positioning, thereby improving the overall functionality of the cartridge 102 and the cartridge carrier 200 system.

The alignment features 406 of one embodiment are distinguishable protrusions present on the inner surface of the cartridge carrier 200. These alignment features 406 serve to guide the cartridge 102 into the correct position within the cartridge carrier 200 when installing a cartridge 102 into the system. These protruding alignment features 406 also help to prevent misalignment and displacement of the cartridge 102 while it is installed and during operation. Notably and as described below in further detail, the alignment features 406 are critical in transitioning an inserted cartridge 102 between the stored and dispensing position.

The alignment features 406 are strategically located within the cartridge carrier 200 in a manner to engage with corresponding features or portions on the cartridge 102. When the cartridge 102 is inserted into the carrier 200, the protruding alignment features 406 guide it into the correct position as the features 406 fit into compatible sections (i.e., alignment channels 408) of the cartridge 102. This results in a snug and correct fit of the cartridge 102 within the cartridge carrier 200.

Furthermore, these alignment features 406 may come in various shapes and sizes and can be constructed using various materials that are suitable for the system and the intended application. They can be rigid to withstand the pressure exerted by the cartridge 102 as it is inserted into the cartridge carrier 200, or flexible to allow for slight variations in cartridge 102 size and shape.

Figure 5A:
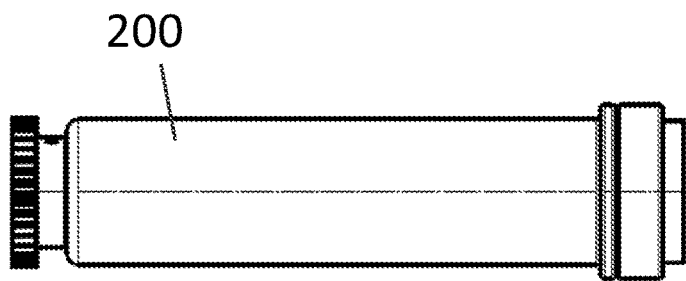
FIG. 5A shows a side-view illustration of the medication cartridge.
Figure 5B:
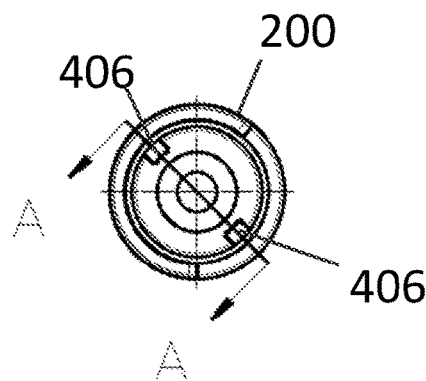
FIG. 5B shows a top-view illustration of the medication cartridge.
Figure 5C:
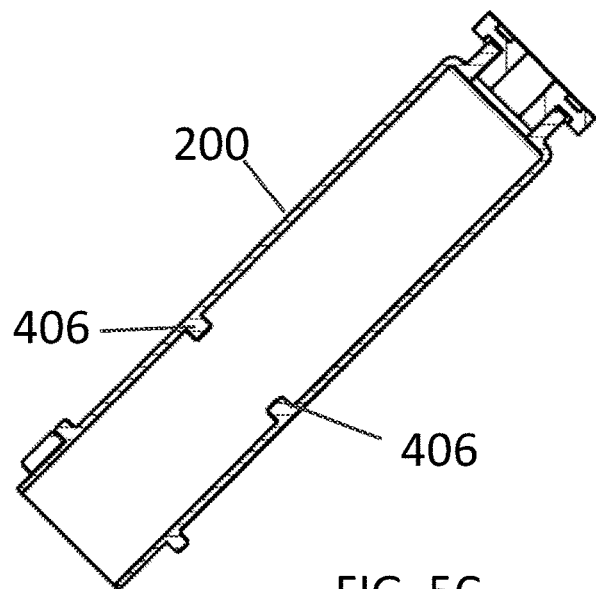
FIG. 5C is a cross-sectional, side-view illustration of the medication cartridge, taken from line A-A of FIG. 5B.

For further understanding, FIGS. 5A through 5C depict side, top, and cross-sectional views, respectively, of the cartridge carrier 200 and alignment features 406. These features 406, protruding into the interior of the cartridge carrier 200, support the accurate placement of cartridges 102 within the device. Thus, the functionality and efficiency of the overall dispensing device 100 are significantly improved along with consistent cartridge 102 performance ensured by these alignment features 406. This inventive cartridge carrier 200 system design genuinely adds value to applications where precise alignment of cartridges 102 in their carrier systems is crucial. This one embodiment indeed ensures an innovative update for improving the efficiency of cartridge insertion and alignment in cartridge carrier systems, potentially paving the way for advancements in devices utilizing such systems.

As noted above and referring again to FIG. 4, the present disclosure also provides a unique medication cartridge 102 that can be inserted within a cartridge carrier, thus providing a novel means to carry, store and administer medication. The essence of this one embodiment lies in the exclusive design of the medication cartridge 102 and the cartridge carrier that is not only easy to operate but also provides secure storage and effortless administration of the medication.

The medication cartridge 102 is an integral part of the inventive concept and is designed to contain distinct types of medications, be it in liquid, gel, or cream, or other dispensable forms of medication. The cartridge 102 can be made up of pharmaceutically safe materials ensuring no chemical reactions occur when in contact with the medication. The cartridge 102, itself can showcase cylindrical or other geometrical shapes as required by shape of the cartridge carrier 200. The medication cartridge 102 and cartridge carrier 200 partnership provides an ideal solution in various medical environments, such as hospitals, pharmacies, nursing homes, or even domestic settings. It proves to be beneficial where multiple medications should be stored and administered safely and hygienically. It combines innovation with convenience, improving medication storage, and administration methodologies.

As noted above and as shown in FIG. 6, the cartridge 102 itself is also designed to provide a marked improvement over other medication containers. It is envisioned to include markings or identification systems for easily recognizing the type of medication stored within each cartridge 102. The real innovation lies in the incorporation of one or more channels 408 and aligned slots 606 within the cartridge 102. These are constructed meticulously within the cartridge 102 and serve a distinct function of aligning and receiving one or more alignment features 406. As will be evident below, these channels 408 and slots 606 engage with the aforementioned alignment features 406 to allow for controlled operation of the device 100.

Figure 6:
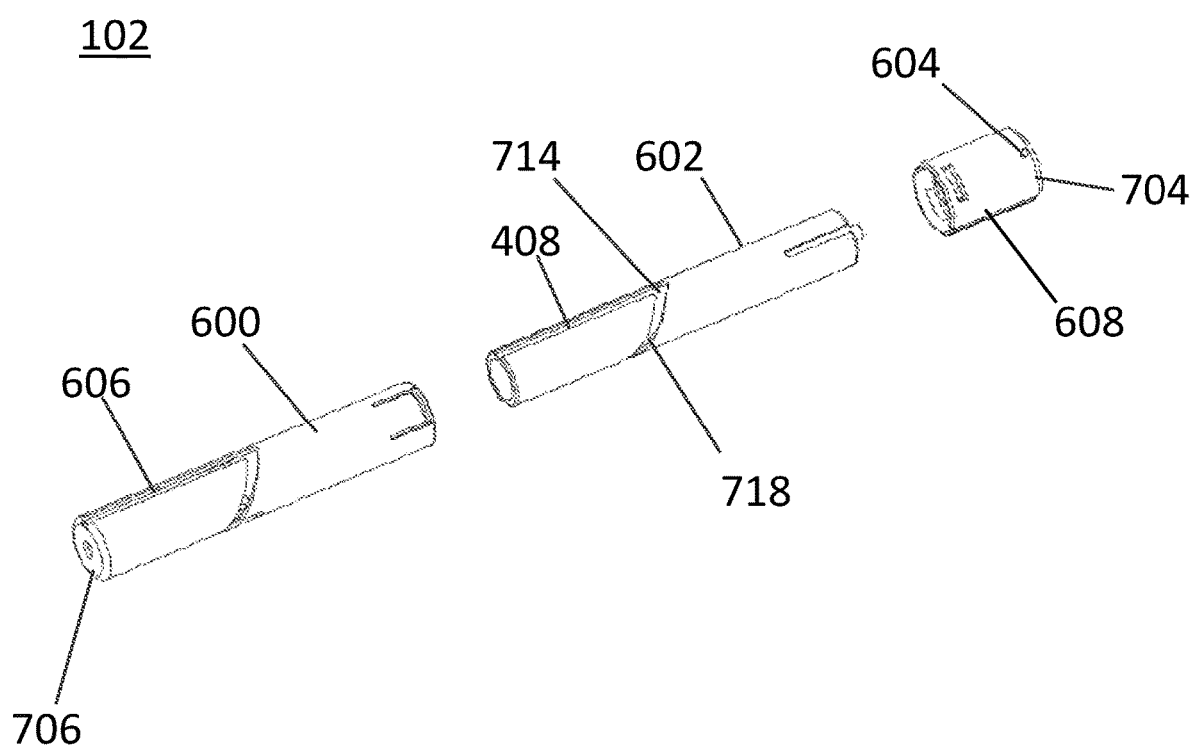
FIG. 6 shows an exploded-view illustration of the medication cartridge.
Figure 7A:
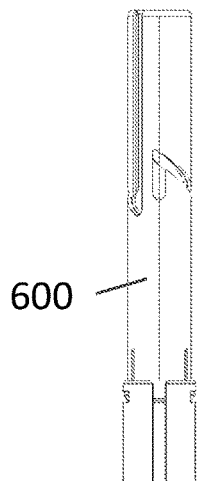
FIG. 7A shows a front-view illustration of the medication cartridge.
Figure 7F:
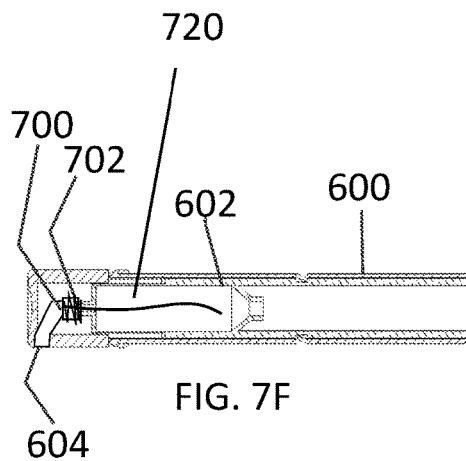
FIG. 7F is a cross-sectional, side-view illustration of the medication cartridge, taken from line A-A of FIG. 7C.
Figure 7B:
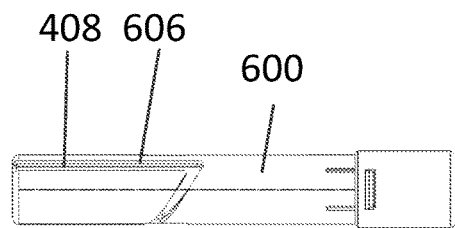
FIG. 7B shows a right, side-view illustration of the medication cartridge.
Figure 7E:
FIG. 7E shows a top-view illustration of the medication cartridge.
Figure 7C:
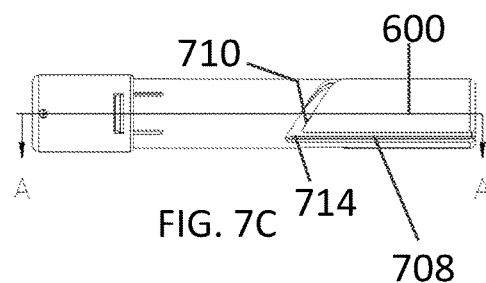
FIG. 7C shows a left, side-view illustration of the medication cartridge.
Figure 7D:
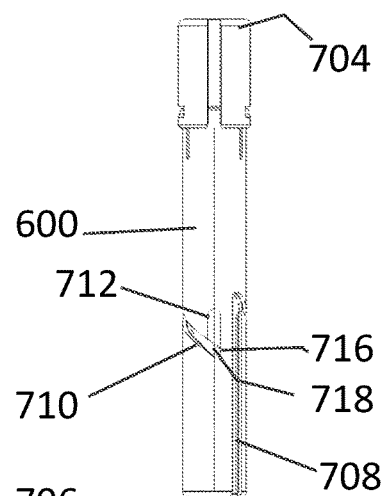
FIG. 7D shows a rear-view illustration of the medication cartridge.

Further and as shown throughout FIGS. 6 through 7F, the present disclosure provides an improved configuration for a medication cartridge 102, particularly advantageous for medications that require enhanced storage for securely maintaining their efficacy and quality. The innovative design of the medication cartridge 102 includes a robust shell 600 that has a dispensing aperture 604 designed for the release of the medication stored within a medication vial 602.

The shell 600, formed from long-lasting and reliable material (e.g., plastic, metal, etc.), is shaped to house the vial 602 securely and efficiently. This shell 600 acts as a protective layer for the vial 602 placed inside, while maintaining the required conditions for the preservation of the medication. The dispensing aperture 604 deployed on the shell 600 is engineered in a way to align with the outlet 702 of the vial 602, ensuring precise and mess-free dispensation of the medication.

Inside the shell 600 is a medication vial 602, which is shaped and positioned in a manner that it can slide without difficulty within the shell 600. This ability of the vial 602 to slide enables convenient load and unload of the medication. The vial 602 includes a pump assembly 700 that is equipped with an outlet 702. The design and positioning of this outlet 702 are such that it aligns perfectly with the dispensing aperture 604 on the shell.

Figure 7G:
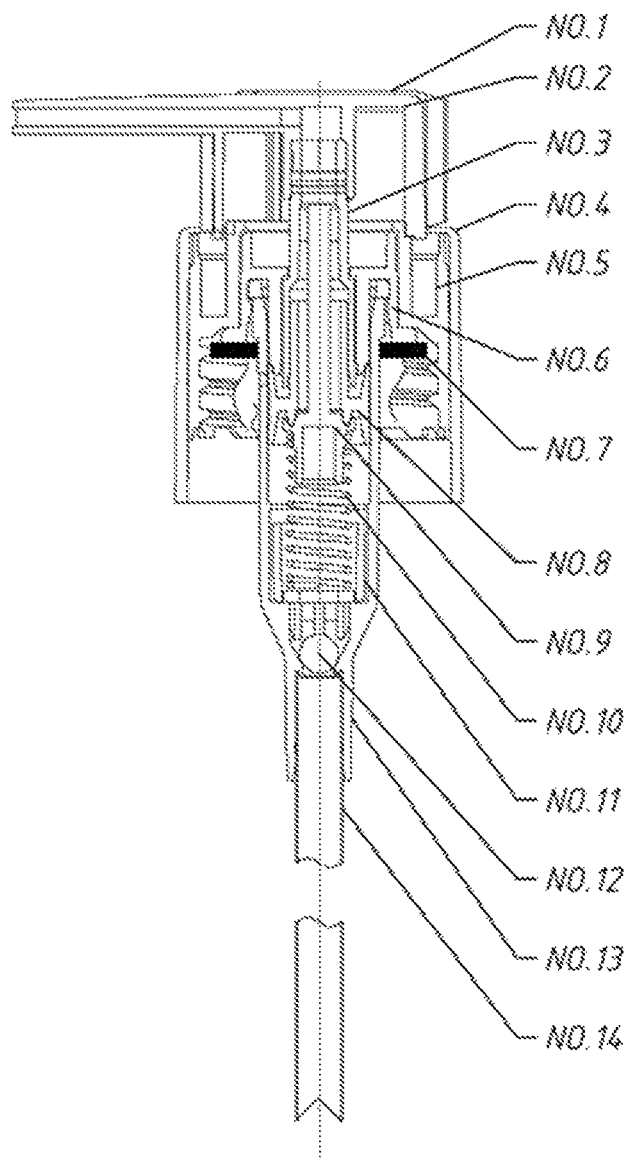
FIG. 7G is an illustration of a lotion pump assembly of the prior art.
Figure 7H:
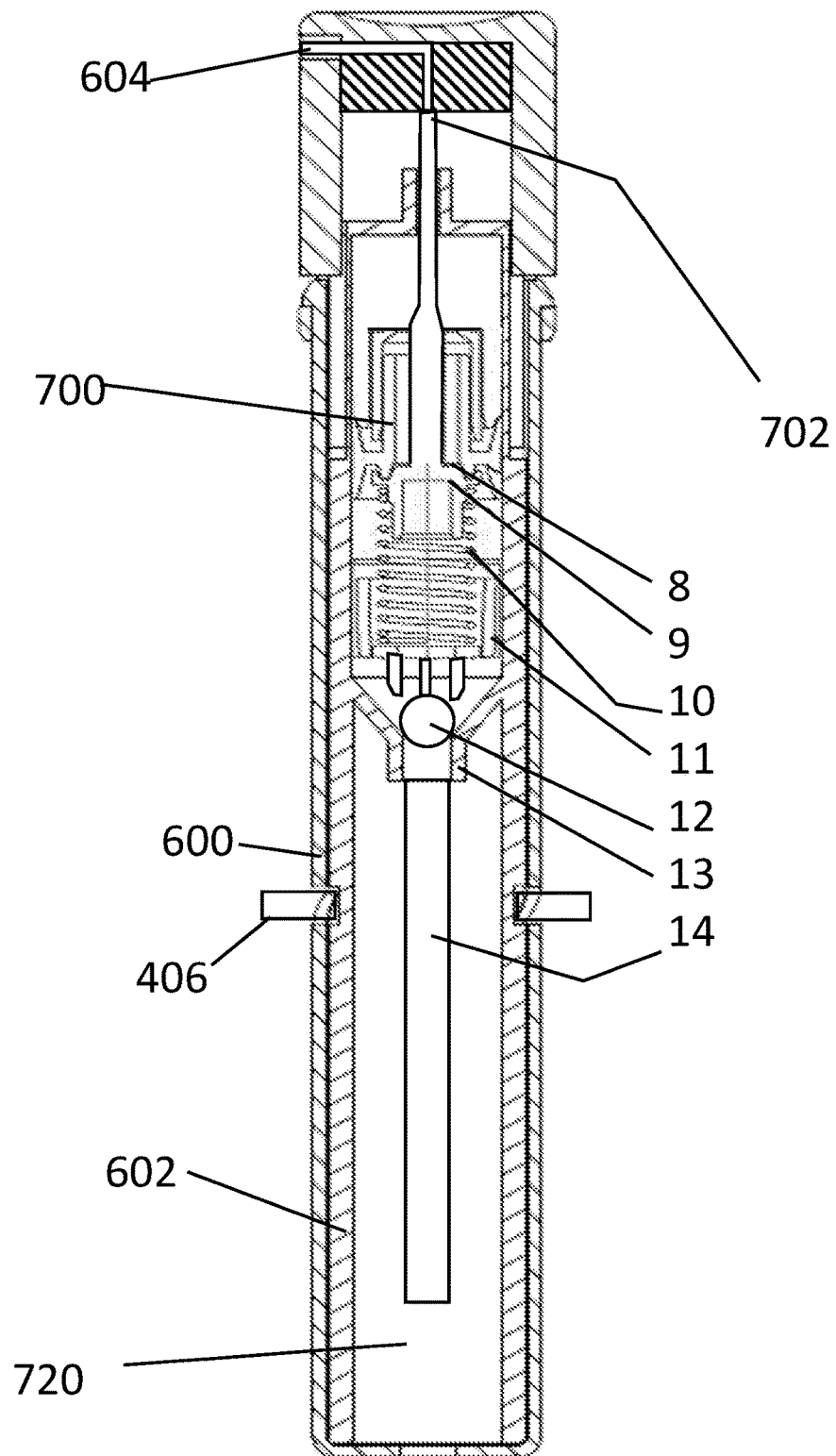
FIG. 7H is an illustration of an example pump assembly as applied to the medication cartridge in accordance with various embodiments of the present invention.

The pump assembly 700 is any suitable assembly that can be affixed with a container (i.e., the vial 602) to allow for pumping or otherwise dispensing a medication or fluid therefrom, a non-limiting example of which includes a compression or spring-loaded pump, similar to the pump mechanism as used in a standard lotion bottle. For reference, FIG. 7G provides an illustration of an example pump assembly as provided for in the prior art, while FIG. 7H provides a non-limiting example of the pump assembly as modified and applied to the present invention. The pump assembly of the prior art (as shown in FIG. 7G) includes a clamp 1, press head 2, press lever 3, coat 4, screw cap 5, connect cap 6, gasket 7, piston 8, piston seat 9, spring 10, spring seat 11, valve 12, housing 13, and a straw 14. As applied to the present invention (as depicted in FIGS. 7F and 7H), the pump assembly 700 is connected to the vial 602, while the shell 602 serves as the press head that is used to press down the piston 8 to force the fluid through the straw 14 and out of the dispensing aperture 604. In some instances the pump assembly 700 can be screwed onto the vial 602; however, it should be understood that the invention is not intended to be limited thereto as the pump assembly 700 can be attached in any suitable manner between the vial 602 and shell 600 to allow for dispensing fluid from the vial 602 and out of the dispensing aperture 604. Further, it should be understood that the specific pump assembly 700 as depicted in FIG. 7H is provided as a non-limiting example of a suitable pump assembly and that the invention is not intended to be limited thereto as other mechanisms or assemblies can be used to dispense the fluid upon actuation. For example, the pump assembly can be formed as an airless pump, a peristaltic pump, a diaphragm pump, a pressurized canister style pump, or any other configuration in which activation of the assembly causes the fluid to dispense.

For illustrative purposes in comparison to a lotion bottle, the vial 602 would serve as the container to hold the fluid, while the shell 600 serves as the pump head that can be depressed to pump the fluid, with the various components of the pump assembly 700 positioned therebetween. In operation and when the medication cartridge 102 is moved to the dispensing position, the alignment features 406 operate to hold the vial 602 in place (due to their locking position in the channel terminal as described in further detail below), while a user can selective press the shell 600 downward around the vial 602 to activate the pump assembly 700 and force fluid from the vial 602.

For example, the vial 602 includes a reservoir 720 in which the medication is stored. The medication can be in a gas or fluid form; however, desirably and in one aspect, the medication is fluid and can be squirted from the medication cartridge 102 (and vial 602) via actuation of the pump assembly 700. As apparent from the description further below, the pump assembly 700 can be easily operated to cause the medication to be dispensed from the vial 602 through its outlet 702. When a force is applied on the pump assembly 700, it triggers the release of the medication inside of the vial 602, causing the medication to travel from the vial 602, passing through the aligned outlet 702 and dispensing aperture 604, where it is released to the user.

As noted above, the pump assembly 700 is any suitable assembly, mechanism, or device that can be affixed with the vial 602 to allow for selective dispensing therefrom. As can be appreciated by those skilled in the art, a non-limiting example of such a pump assembly 700 is a spring-loaded system utilizing a stacked one-way valve system to temporarily create a vacuum, allowing fluid to be aspirated from the reservoir 720 and dispensed through the outlet 702 and dispensing aperture 604 upon depression of the shell 600 around the vial 602.

As noted above, the medication cartridge 102 is generally formed of two components, a shell 600 and a medication vial 602. The vial 602 is sized to be secured within and slide within the shell 600. As shown, the medication cartridge 102 includes a top end 704 and a bottom end 706. Although the shell 600 in FIG. 6 is illustrated as having a cap component 608 at the top end 704, the invention is not intended to be limited thereto as the shell 600 can be formed such that the cap component 608 is integrally formed with the shell 600 as a single unit. In such an aspect, a hole (e.g., sealable hole) can be formed at the bottom end 706 (or top end 704) of the shell 600 to allow for insertion of the vial 602 into the shell 600.

Notably and of particular importance, the vial 602 includes channels 408 that are aligned with the slots 606 on the shell 600. These channels 408 and slots 606 are built in a manner to accurately align with the alignment features 406 of the cartridge carrier 200. The number and size of these channels 408 and slots 606 can vary depending on the number of alignment features 406 intended to be placed therein. These channels are purposefully built to receive these alignment features, allowing secure and precise positioning. This design ensures that the alignment features do not shift their placement, further guaranteeing the stabilization of the medication within the cartridge.

For example, one example embodiment includes a structure involving a pair of opposing channels 408 are formed on opposite sides of the vial 602. These channels 408 are typically parallel to each other, though variations can occur. In one aspect, each of the pair of opposing channels 408 originates from the lowermost end or bottom end 706 of the vial 602. The pair of opposing channels 408 rise upward from this point, extending towards the top end 704 of the vial 602. This ascension continues until they reach a point known as the first junction 714. It must be clarified that this first junction 714 is not an arbitrary point but is a strategically designed and located structural feature within the device to precisely position the cartridge 102 between stored and dispensing positions.

Once these channels 408 have reached the first junction 714, the trajectory shifts. At this point, the channels 408 do not continue with the upward gradient. Instead, they commence a downward traversal toward the bottom end 706. They proceed downwards, but not vertically downwards. This descent is carried out on an angle around the vial 602, intended to enhance function and performance.

These angled downward channels 408 continue to move in the said direction until they reach an area deemed as the second junction 716. It is at this point that these channels 408 cease to continue. They terminate at this juncture, each channel 408 ending in what is referred to as a channel terminal 718. As will be apparent below, this distinctive configuration of the channels 708 enables them to perform their intended purpose more efficiently. It is important to consider the precise and specific architectural design of these channels 408, including their starting point at the bottom end 706 of the vial 602, their rise towards the first junction 714, their angled descent towards the second junction 716, which with respect to the channels, is the final termination at the channel terminal 718. These particular design elements reveal a thoughtful consideration of their role within the device and contribute both independently and collectively to the overall functionality and performance of the device or system in question.

The present disclosure also provides an embodiment which is characterized by a pair of opposing slots 606 in the shell 600 that align with the pair of opposing channels 408. More specifically, one embodiment is the configuration and interaction of these parts, enabling the pair of opposing protrusions 406 to pass through the pair of opposing slots 606 and into the pair of opposing channels 408 to allow for moving the cartridge 102 between the stored and dispensing positioned and, ultimately, sliding the vial 602 within the shell 600 for dispensation of the medication.

The pair of opposing slots 606 are formed through the surface of the shell 600 to allow access to the channels 408 therein. These slots 606 are designed with precise measurements to fit and accommodate corresponding elements, namely, a distinct pair of opposing protrusions 406. The opposing slots 606 are carved or formed into the shell 600 and aligned in such a way that they maintain a clear, unobstructed path for the protrusions 406 to pass through them with ease. The unique arrangement allows for the insertion of the pair of opposing protrusions 406, which are another critical characteristic of this one embodiment. These protrusions 406, with their matching dimensions to the slots 606, are designed to glide smoothly through the opposing slots 606 and into the aligned opposing channels 408. The path provided by the slots 606 guides and directs the protrusions 406 into the appropriate channels 408. Consequently, this ensures a specific interaction between the three parts: the opposing protrusions 406 smoothly pass through the opposing slots 606, and they are then guided into the opposing channels 408, maintaining a suitable and secure connection.

Further, the medication cartridge 102 presents an innovative design with respect to the pair of opposing slots 606. Each of the pair of opposing slots 606 is formed of a first slot 708, a second slot 710, and a third slot 712. These slots are strategically positioned and oriented for the optimal functioning of the device. The first slot 708 in each pair begins at the bottom end 706 of the shell 600 and extends upward toward the top end 704. It is arranged in such a way that it mandates a route which ascends from the base to a designated position along the length of the cartridge 102, otherwise referred to as the first junction 714.

Subsequent to the first junction 714, the structure of the shell 600 features a second slot 710 for each pair. Instead of following the upward trajectory of its predecessor, this second slot 710 takes on a unique characteristic of its own by providing an angled path that descends from the first junction 714. This downward movement proceeds until it reaches a designated point along the body of the shell 600, referred to herein as the second junction 716. Moreover, the slot design of the shell 600 reverts back to an upward direction in the subsequent and final arrangement of each pair—the third slot 712. Commencing from the second junction 716, this slot ascends once again (e.g., vertically) towards the top end 704 of the cartridge. The distinct positions and paths of the slots 708, 710, and 712 provide a sophisticated layout that enhances the fundamental operations of this medication cartridge 102. Notably, while the channel 408 terminates at the second junction 716 or channel terminal 718, the third slot 712 proceeds upwards from the second junction 716. This differentiation allows for the selective dispensing of the medication therein. This innovative structure enhances the controlled dispensing of medication, making this cartridge 102 particularly advantageous in the administration of drugs. The angles and special slot layout improves the overall efficiency and operational effectiveness of the delivery system, which in turn can broaden its potential applications in the medical and pharmaceutical fields. The precise orientation of the slots from bottom to top and their alternating directions contribute to creating a balanced and smooth transition of the medication within the cartridge 102. The level of control provided by this inventive structure is a significant evolution in medication delivery system designs.

Figure 8A:
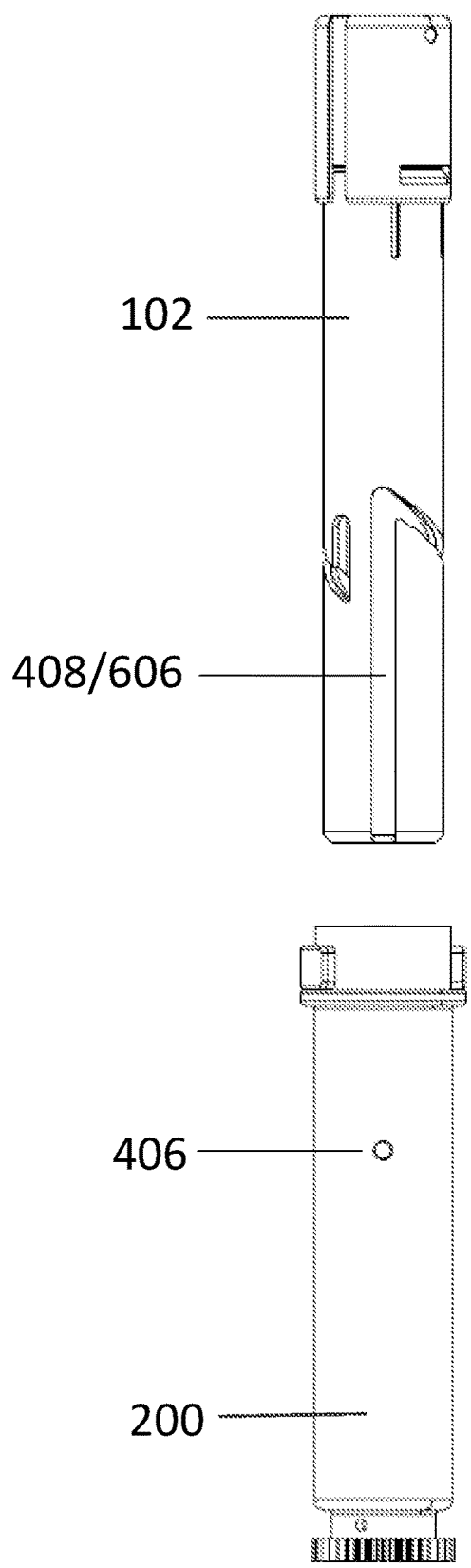
FIG. 8A shows an exemplary illustration of the cartridge carrier and medication cartridge.
Figure 8B:
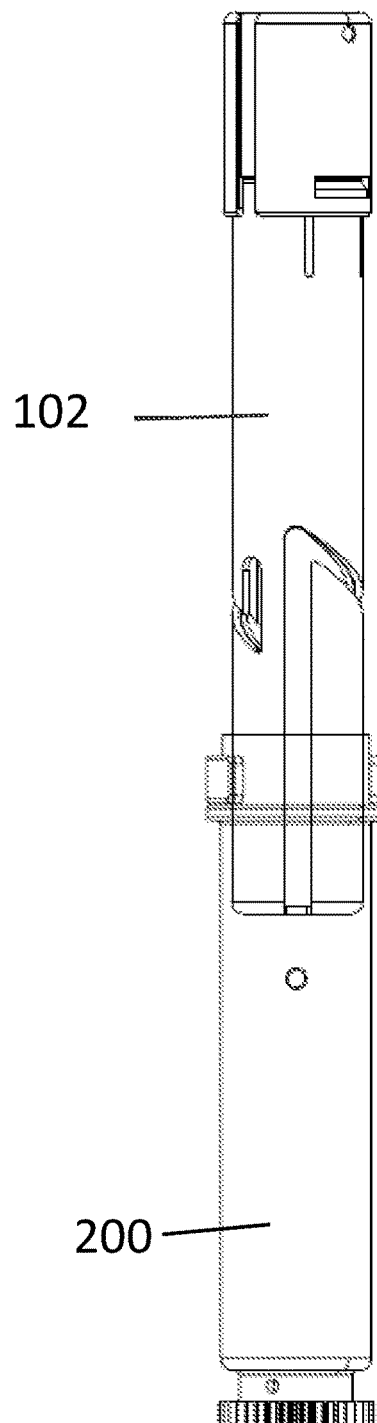
FIG. 8B shows an exemplary illustration of the cartridge carrier and medication cartridge, depicting the medication cartridge as being inserted into the cartridge carrier.
Figure 9:
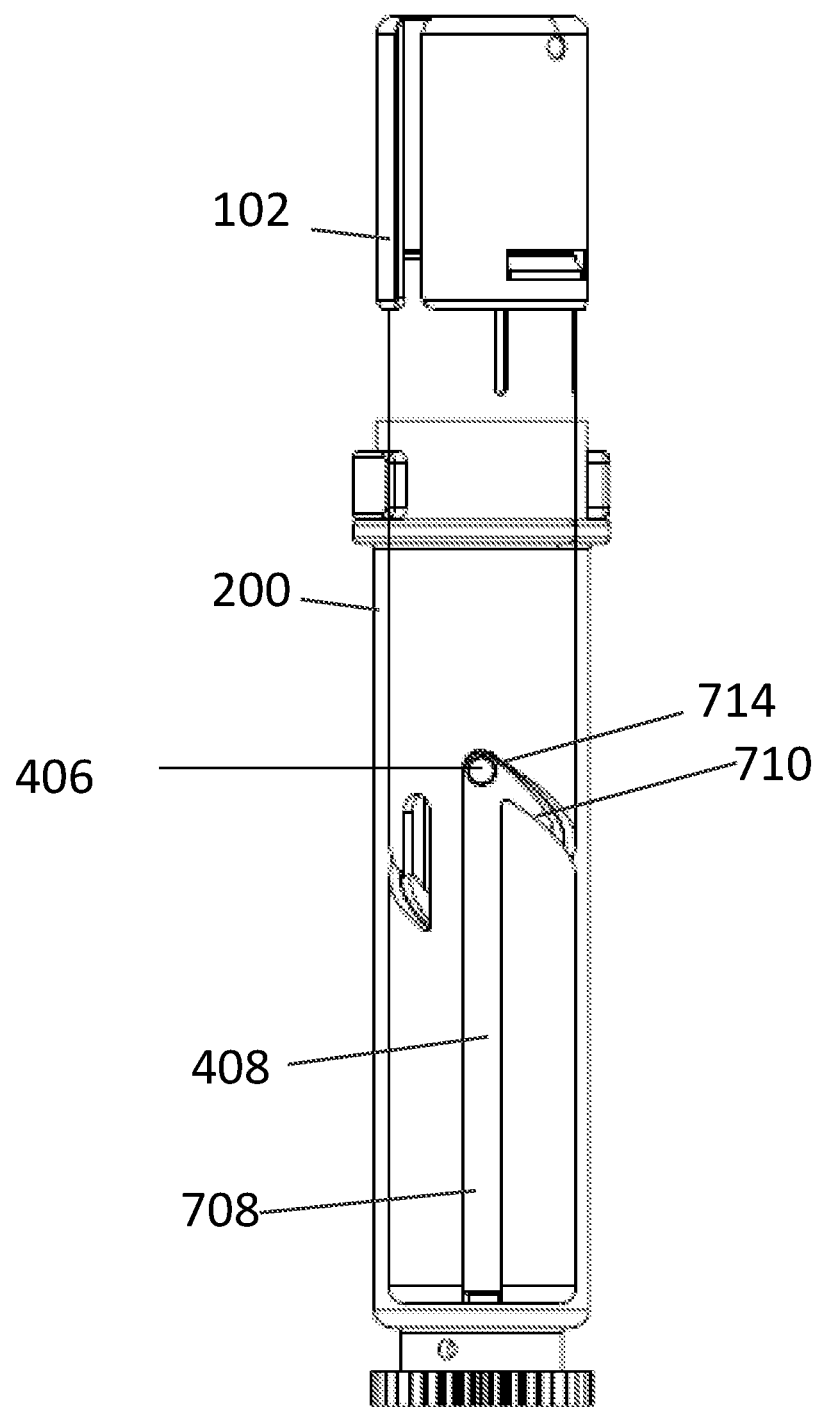
FIG. 9 shows an exemplary illustration of the medication cartridge inserted into the cartridge carrier.

For further understanding, FIGS. 8A and 8B depict a medication cartridge 102 as being installed or otherwise inserted into the cartridge carrier 200. As shown, the alignment features 406 (i.e., opposing protrusions) provided a keyed connection and alignment by passing through the channels 408 and slots 606 to allow the cartridge 102 to be contained within the carrier 200. As shown in FIG. 9, the alignment feature 406 has travelled through the first slot 708 and channel 408 to rest at the first junction 714. In this position, the medication cartridge 102 is held within the dispensing device in a stored position. Since the alignment feature 406 is at a fixed location within the cartridge carrier 200, and because the second slot 710 and channel 408 descend downwards at an angle from the first junction 714, rotation of the cartridge carrier 200 necessarily forces the medication cartridge 102 upwards within the cartridge carrier 200. These aspects are further depicted in FIGS. 10A through 10C.

FIG. 10A depicts the medication cartridge in a stored position. As shown, the alignment feature 416 rests within the first junction 714. As shown in FIG. 10B, rotation 1000 (via the gear wheel 404) of the cartridge carrier 200 forces the alignment feature 416 to traverse through the second slot 710 and channel 408 away from the first junction 714. In doing so and as shown, the medication cartridge 102 is lifted upwards within the cartridge carrier 200. Further rotation 1000 of the cartridge carrier 200, as shown in FIG. 10C, results in the alignment feature 416 to traverse until it rests within the second junction 716 and the channel 408 terminates at the channel terminal 718. Notably, when the alignment feature 416 is at the second junction 716, the medication cartridge 102 is lifted from the dispensing device 100 into the dispensing position. Thus, the journey of the protrusions commences from the first junction 714, progressing towards the second junction 716. As a consequence of this carefully guided pathway, the medication cartridge 102 experiences an upward shift. This movement is instrumental in the transition of the medication cartridge 102 from what is denoted as the 'stored position' to its final location, the 'dispensing position'.

Figure 11C:
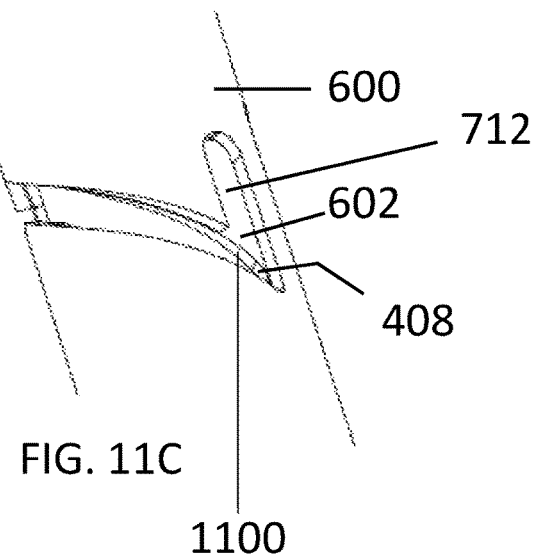
FIG. 11C shows an exemplary illustration of the medication cartridge, depicting the vial within the shell.
Figure 11A:
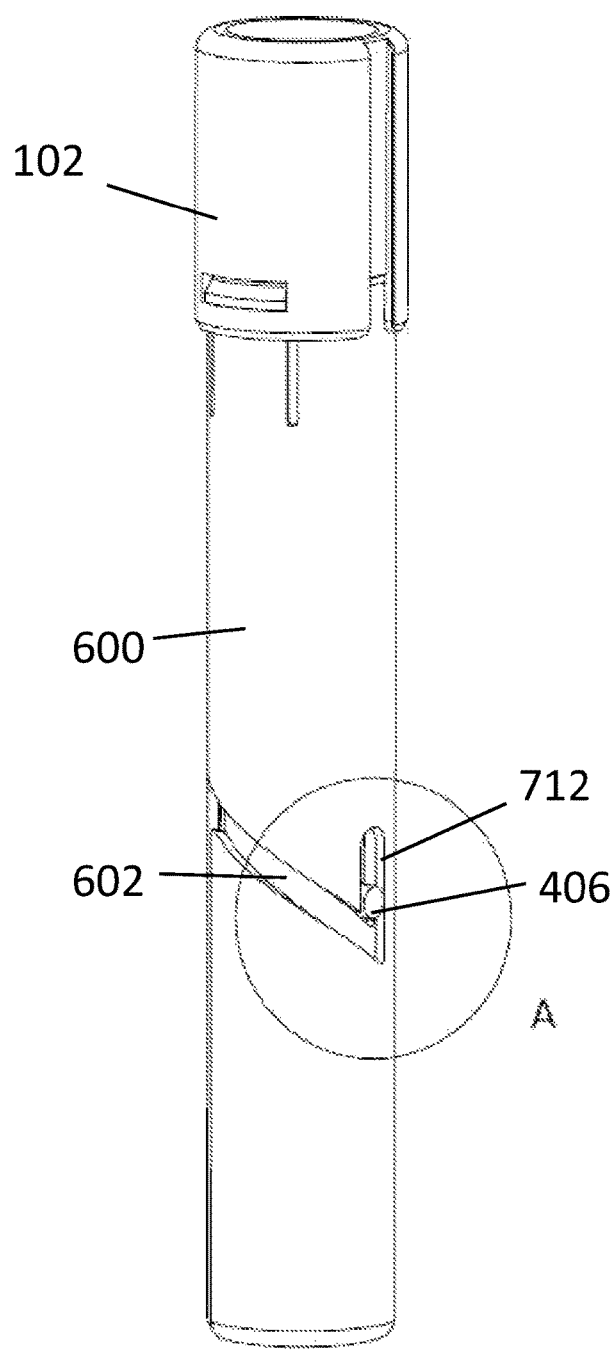
FIG. 11A shows an exemplary illustration of the medication cartridge, depicting the vial sliding within the shell.
Figure 11B:
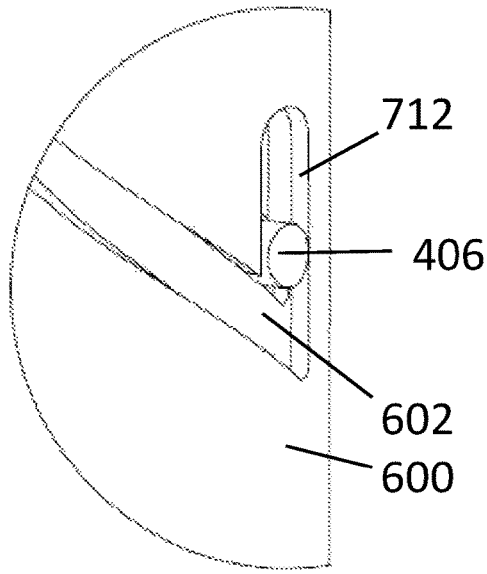
FIG. 11B shows close-up view of Detail A, taken from FIG. 11A.

While the cartridge 102 is in the dispensing position, the vial 602 therein is in the expanded state and ready to be compressed to dispense medication. As shown in FIGS. 11A through 11C, although the channel 408 in the vial 602 has terminated, the slot in the shell 600 continues upwards as the third slot 712. Thus, when the medication cartridge 102 is in the dispensing position, a user can selectively press down on the medication cartridge 102 to cause the vial 602 to slide within the shell 600. As shown in FIG. 11C, due to the stepped inner wall 1100 and end of the channel 408, the vial 602 is held in place by the alignment features 406 and only the outer shell 600 can travel downward when pressed down, causing the shell 600 to slide downward over the vial 602 and allowing the pump assembly to be actuated and spray/dispense the medication. This feature is further illustrated in FIGS. 12A and 12B. As shown, pressing downward 1200 on the medication cartridge 102 causes the alignment features 406 to travel upwards through the third slot 712, thereby forcing the shell 600 downward while holding the vial 602 in place. While the shell 600 is forced downward, it compresses the vial 602 from the expanded to compressed state. The transition from the expanded to compressed state activates the pump assembly to force medication 1202 from the vial 602 and through the dispensing aperture 604, similar to a squirt of medication. The pump assembly can be configured as a spring-loaded pump mechanism that lifts the shell 600 after being compressed, thereby returning the alignment features 406 to the second junction 716. Once dispensed, the dispensing device 100 and associated activator mechanism 300 can be activated to turn the gear wheel 404 in an opposite direction as previously rotated. Such a rotation lowers the medication cartridge 102 back to the stored position as the alignment features 406 are forced back to the first junction 714 (shown in FIG. 10A).

In one aspect, the device 100 is formed to sense once a predetermined number of squirts (e.g., one, etc., as prescribed) have been initiated so that it automatically activates the activator mechanism 300 to return the medication cartridge 102 back to the stored position, thereby retracting the medication cartridge 102 and inaccessibility after user. For example, magnetic sensors, a trigger, electrical sensors, light sensors, or any other means for determining if medication has been dispensed from the vial 602 can be included within the device 100. As a non-limiting example, a magnet can be positioned at the bottom of the shell 600 while a magnetic reed switch is similarly positioned at the bottom of the cartridge carrier 200. Pressing the medication cartridge 102 and its shell 600 downward within the cartridge carrier 200 brings the magnet into close proximity of the magnetic reed switch to notify the associated electronics (integrated circuit, etc.) that a single squirt has been dispensed. After the predetermined number of squirts, the activator mechanism is activated to rotate the cartridge carrier 200 and return the medication cartridge 102 to the stored position to prevent further and unauthorized use. In another aspect, the device 100 can be include any necessary components (integrated circuit, etc.) to allow for a timed configuration in which the medication cartridge 102 is held in the dispensing position. For example, the device 100 can be programmed such that after authentication and movement of the medication cartridge 102 in the dispensing position, it is returned to the stored position after a predetermined or preprogrammed amount of time (e.g. 2 seconds, etc.).

As noted above, a unique design feature allows for the vial 602 to exist in two distinct states; namely an expanded state and a compressed state. The transition between these two stages is critical to the functionality of the device. When it moves from the expanded state towards the compressed state, the incorporated pump assembly 700 is triggered into action. This incorporation of a pump assembly 700 and its associated operation indicates an upbeat sophistication of the one embodiment, going beyond traditional static medical dispensing devices. The purpose of this actuation is specifically to ensure the controlled release of the medicine within the vial 602. On the actuation of the pump assembly 700, the medicine 1202 is pushed out of the vial's 602 outlet. This outflow proceeds under the controlling and moderating role of the pump assembly 700, guaranteeing a controlled and managed release of the medicine.

In summary, the present disclosure provides an innovative medication dispensing device 100. The core of this medication dispensing device 100 revolves around a unique cartridge carrier 200 design, integrated with a pair of opposing protrusions 406 and a uniquely designed medication cartridge that is functionally designed to operate based on the positioning of the protrusions 406 after user authentication. As noted above, in one aspect, the device 100 includes an authentication mechanism 106. Upon successful authentication, the authentication mechanism 106 triggers the activator mechanism 300. In this context, the activation entails the initiation of moving the medication cartridge 102. When activated, it can efficaciously induce the cartridge carrier 200 mechanism to actuate, progressing the inserted medication cartridge 102 from a stored position to a dispensing position. Maximal effectiveness is ensured as the activator mechanism 106 is engendered only after a successful user authentication process, thereby verifying that the medication is dispensed to the appropriate user. This sequence not only ensures secure and controlled dispensing of the medication but also minimizes errors and the potential for unlawful access. In one aspect, the interconnectedness between the authentication mechanism 106 and the activator mechanism 300 forms the crux of this system, thereby augmenting the overall safety and operation of the dispensing device 100. Moreover, this intricate mechanism, in coordination with the user and the cartridge carrier 200, ensures that the process of moving the medication cartridge 102 from a stored position to a dispensing position is not only smooth but also efficient and secure.

Thus, in one aspect, a purpose of this inventive operation is to modify the positioning of the medication cartridge 102 from a state of storage to a dispensing state, thereby facilitating the delivery of medication in a controlled, efficient, and timely manner. The operational process involved in use of the dispensing device 100 advances through several stages, starting with the activation of the activator mechanism 300. The initiation of this mechanism 300 leads to a rotational motion in the cartridge carrier 200, a critical movement that fosters the maneuvering of the pair of opposing protrusions 406 (i.e., alignment features). This rotation is precisely designed to stimulate this movement, making the entire process efficient and seamless. The pair of opposing protrusions 406 are guided in their motion by a pair of opposing slots 606 in conjunction with a pair of opposing channels 408. These channels 408 and slots 606 function in harmony, not only providing a safe passage but also controlling the direction of the movement of these protrusions 406 while guiding the medication cartridge 102 between a stored position and a raised dispensing position. The unique features of the slots 606 and channels 408 also allow a user to compress the vial 602 within the medication cartridge 102 to dispense medication 1202.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A medication dispensing system, comprising:
    a medication dispensing device, the medication dispensing device having a housing with a cartridge carrier therein, the cartridge carrier having a keyed connector that is keyed to a medication cartridge to allow for insertion and alignment of the medication cartridge within the cartridge carrier;

a medication cartridge for insertion within the cartridge carrier;

wherein an activator mechanism is positioned within the housing, the activator mechanism operably connected with the cartridge carrier to cause the cartridge carrier to actuate, whereby upon actuation of the cartridge carrier, the cartridge carrier selectively moves an inserted medication cartridge between a stored position and a dispensing position;

wherein the cartridge carrier is rotatable within the housing;

wherein the cartridge carrier includes a proximal end and a distal end, the proximal end being open for receiving the medication cartridge therein, while the distal end includes a gear wheel operably connected to the activator mechanism;

wherein the activator mechanism includes at least a battery, a motor, and one or more gears that are operably connected to the gear wheel, such that activation of the activator mechanism causes the motor to turn the one or more gears and, in doing so, turn the gear wheel and rotate the cartridge carrier;

wherein the keyed connector includes one or more alignment features that protrude into the cartridge carrier;

wherein the medication cartridge is an elongated cartridge with one or more alignment channels that align with and receive the one or more alignment features;

wherein the one or more alignment channels includes a pair of opposing channels, while the one or more alignment features are a pair of opposing protrusions that slide within the pair of opposing channels;

wherein the medication cartridge is comprised of a shell having a dispensing aperture and a vial slidably positioned within the shell, the vial having a pump assembly with an outlet aligned with the dispensing aperture;

wherein the vial is slidable within the shell between an expanded state and a compressed state, such that when transitioning to the compressed state, the pump assembly is actuated to pump medicine from the outlet and through the dispensing aperture;

wherein the shell includes a pair of opposing slots that align with the pair of opposing channels such that the pair of opposing protrusions pass through the pair of opposing slots and into the pair of opposing channels; and wherein the medication cartridge has a bottom end and a top end, such that each of the pair of opposing slots has a first slot that rises upward from the bottom end toward the top end to a first junction, and then a second slot that traverses downward at an angle from the first junction toward a second junction, and then a third slot that rises upward again from the second junction toward the top end.

2. The medication dispensing system as set forth in claim 1, wherein each of the pair of opposing channels rises upward from the bottom end toward the top end to the first junction, and then traverses downward at an angle from the first junction toward the second junction, where each of the pair of opposing channels terminates in a channel terminal.

3. The medication dispensing system as set forth in claim 2, wherein when the medication cartridge is within the cartridge carrier in the stored position, the pair of opposing protrusions rest within the first junction.

4. The medication dispensing system as set forth in claim 3, wherein activation of the activator mechanism causes a rotation of the cartridge carrier, thereby causing the pair of opposing protrusions to travel through the pair of opposing slots and the pair of opposing channels from the first junction to the second junction and, in doing so, lift the medication cartridge from the cartridge carrier from the stored position to the dispensing position.

5. The medication dispensing system as set forth in claim 4, wherein when in the dispensing position, the pair of opposing protrusions pass through the pair of opposing slots and into the pair of opposing channels at the second junction and rest within the channel terminals.

6. The medication dispensing system as set forth in claim 5, wherein the medication cartridge is formed such that depression of the top end of the medication cartridge forces the shell downward while the pair of opposing protrusions pass through the third slots while remaining affixed within the channel terminals, thereby forcibly sliding the vial within the shell from the expanded state to the compressed state and actuating the pump assembly.

7. The medication dispensing system as set forth in claim 6, wherein the medication dispensing device further comprises an authentication mechanism operably connected with the activator mechanism, the authentication mechanism operable for authenticating a user and, when authenticated, activating the activator mechanism to cause the cartridge carrier to actuate and move the inserted medication cartridge from the stored position to the dispensing position.

* * * * *